(12) United States Patent
Goertz et al.

(10) Patent No.: US 12,053,194 B2
(45) Date of Patent: Aug. 6, 2024

(54) SYSTEMS AND METHODS FOR TREATING VASCULAR OCCLUSIONS WITH CATHETER BASED ULTRASOUND

(71) Applicant: Sunnybrook Research Institute, Toronto (CA)

(72) Inventors: David Goertz, Toronto (CA); Kullervo Hynynen, Toronto (CA); Alex Wright, Toronto (CA)

(73) Assignee: SUNNYBROOK RESEARCH INSTITUTE, Toronto (CA)

( * ) Notice: Subject to any disclaimer, the term of this patent is extended or adjusted under 35 U.S.C. 154(b) by 294 days.

(21) Appl. No.: 16/574,710

(22) Filed: Sep. 18, 2019

(65) Prior Publication Data
US 2020/0107843 A1 Apr. 9, 2020

Related U.S. Application Data

(60) Provisional application No. 62/741,259, filed on Oct. 4, 2018.

(51) Int. Cl.
*A61B 17/22* (2006.01)
*A61B 8/12* (2006.01)
*A61B 17/00* (2006.01)

(52) U.S. Cl.
CPC ............ *A61B 17/2202* (2013.01); *A61B 8/12* (2013.01); *A61B 2017/0003* (2013.01);
(Continued)

(58) Field of Classification Search
CPC .................. A61B 17/2202; A61B 8/12; A61B 2017/0003; A61B 2017/2208;
(Continued)

(56) References Cited

U.S. PATENT DOCUMENTS 5,735,811 A * 4/1998 Brisken ............ A61B 17/22012
604/22
6,312,402 B1 * 11/2001 Hansmann ......... A61B 17/2202
600/437
(Continued)

OTHER PUBLICATIONS

Aronov, B. S. et al. Experimental investigation of coupled vibrations in piezoelectric cylindrical shells. J. Acoust. Soc. Am. 120 3, Sep. 2006.
(Continued)

*Primary Examiner* — Sean A Frith
(74) *Attorney, Agent, or Firm* — HILL & SCHUMACHER

(57) ABSTRACT

A system and method is provided for generating ultrasound at the tip of an intravascular catheter. This may be used for the treatment of vascular occlusions, including chronic total occlusions (CTOs) and thrombotic occlusions (e.g., deep vein thrombosis, stroke, myocardial infarction). For instance, the systems and methods may be used to induce cavitation to enhance the enzymatic degradation of a vascular occlusion. In some configurations, the approach employs a hollow cylindrical transducer, electrically stimulated in the radial direction at a frequency corresponding to the length mode excitation, thereby projecting ultrasound forwards past the catheter tip. This design overcomes electrical impedance issues for the generation of low frequencies with a smaller diameter transducer capable of negotiating a coronary artery. The hole within the transducer may accommodate a guidewire to facilitate its placement adjacent to the proximal portion of the occlusion.

46 Claims, 14 Drawing Sheets

(52) U.S. Cl.
CPC .............. *A61B 2017/22008* (2013.01); *A61B 2017/22021* (2013.01); *A61B 2017/22028* (2013.01); *A61B 2017/22038* (2013.01); *A61B 2017/22079* (2013.01); *A61B 2017/22088* (2013.01); *A61B 2017/22089* (2013.01)

(58) Field of Classification Search
CPC ........... A61B 2018/22021; A61B 2017/22028; A61B 2017/22038; A61B 2017/22079; A61B 2017/22088; A61B 2017/22089
See application file for complete search history.

(56) References Cited

U.S. PATENT DOCUMENTS

| | | | |
|---|---|---|---|
| 6,457,365 B1* | 10/2002 | Stephens | A61B 8/12 600/463 |
| 6,863,653 B1* | 3/2005 | Zanelli | A61B 18/20 600/437 |
| 8,021,660 B2 | 9/2011 | Strauss | |
| 8,454,520 B2 | 6/2013 | Van Der Steen | |
| 8,622,911 B2 | 1/2014 | Hossack | |
| 9,192,566 B2 | 11/2015 | Soltani | |
| 9,387,515 B2 | 7/2016 | Hynynen | |
| 9,561,073 B2 | 2/2017 | Ogata | |
| 2001/0041880 A1* | 11/2001 | Brisken | A61N 7/022 604/503 |
| 2005/0197619 A1* | 9/2005 | Rule | B08B 9/00 601/2 |
| 2006/0241524 A1* | 10/2006 | Lee | A61B 18/1492 601/2 |
| 2009/0112150 A1* | 4/2009 | Unger | A61M 37/0092 604/22 |
| 2011/0121687 A1* | 5/2011 | Aoki | B06B 1/0677 310/334 |
| 2011/0301506 A1* | 12/2011 | Volz | A61B 17/2202 601/2 |
| 2013/0197555 A1* | 8/2013 | Schaer | A61B 17/12045 606/170 |
| 2013/0253387 A1* | 9/2013 | Bonutti | A61B 17/24 601/46 |
| 2014/0073995 A1* | 3/2014 | Teofilovic | A61B 17/22004 601/2 |
| 2014/0148832 A1* | 5/2014 | Walton | A61B 17/2202 606/169 |
| 2016/0008636 A1* | 1/2016 | Warnking | A61B 8/483 600/411 |
| 2016/0045771 A1* | 2/2016 | Kohler | A61B 5/055 606/27 |
| 2016/0082243 A1* | 3/2016 | Genstler | A61B 34/20 604/22 |
| 2016/0270806 A1* | 9/2016 | Wallace | A61B 17/22012 |
| 2017/0290598 A1* | 10/2017 | Culbert | A61B 17/22 |
| 2018/0154123 A1* | 6/2018 | Werneth | A61F 2/966 |

OTHER PUBLICATIONS

Colmenarez, H. J. et al., Efficacy and safety of drug-eluting stents in chronic total coronary occlusion recanalization: a systematic review and meta-analysis, J American College Cardiol, 55:1854-1866, 2010.
Dixon, AJ et al. 2018. In Vitro Sonothrombolysis Enhancement by Transiently Stable Microbubbles Produced by a Flow-Focusing Microfluidic Device. Annals of biomedical engineering 46 (2), 222-232.
Sun, D, et al. Axial vibration characteristics of a cylindrical, radially polarized piezoelectric transducer with different electrode patterns, Ultrasonics 50:403-410, 2010.
Fefer, P. et al., Current perspectives on coronary chronic total occlusions: the Canadian Multicenter Chronic Total Occlusions Registry, J American College Cardiology, 59:991-997 (2012).
Galassi AR, et al., Long-term clinical and angiographic results of sirolimus-eluting stent in complex coronary chronic total occlusion revascularization: the SECTOR registry. J Interv Cardiol, 24:426-436, 2011.
George S, et al., Long-term follow-up of elective chronic total coronary occlusion angioplasty: analysis from the U.K. Central Cardiac Audit Database. J Am Coll Cardiol, 64:235-243, 2014.
Goertz, David E., et al. "In vivo feasibility study of ultrasound potentiated collagenase therapy of chronic total occlusions." Ultrasonics 54.1 (2014): 20-24.
Grantham J, et al., Chronic total occlusion angioplasty in the United States, J American College Cardiology Cardiovascular Interventions, 2:479-486, 2009.
Hoebers LP, et al., Contemporary overview and clinical perspectives of chronic total occlusions, Nature Rev Cardiology, 11:458-469, 2014.
Hynynen K, et al. Lateral Mode Coupling to Reduce the Electrical Impedance of Small Elements Required for High Power US Therapy Phased Arrays, IEEE Trans Ultrasonics Ferroelect Freq Control, 56: 557-564, 2009.
Jaffe R., et al., Natural history of experimental arterial chronic total occlusions, Journal of the American College of Cardiology, 53:1148-1158, 2009.
Keeley, E. C., et al., Primary angioplasty versus intravenous thrombolytic therapy for acute myocardial infarction: a quantitative review of 23 randomised trials. Lancet, 361:13-20, 2003.
Kim, J., et al. "Intravascular forward-looking ultrasound transducers for microbubble-mediated sonothrombolysis." Scientific reports 7.1 (2017): 3454.
Kirschbaum SW, et al., Evaluation of left ventricular function three years after percutaneous recanalization of chronic total coronary occlusions, Journal American College Cardiology 101:179-185, 2008.
Lauterborn W, et al. Experimental approach to a complex acoustic system, International J Bifurcation Chaos, 3:635-642, 1993.
Prasad A, et al., Trends in outcomes after percutaneous coronary intervention for chronic total occlusions: a 25-year experience from the Mayo Clinic, J American College Cardiology, 49:1611-1618, 2007.
Saalbach, K-A et al. Self-sensing cavitation detection in ultrasound-induced acoustic cavitation. Ultrasonics vol. 94, Apr. 2019, pp. 401-410.
Safley DM, et al., Quality of life benefits of percutaneous coronary intervention for chronic occlusions. Catheter Cardiovasc Interv, 84:629-634, 2014.
Song JH, et al. Feasibility of Using Lateral Mode Coupling Method for a Large Scale US Phased Array for Noninvasive Transcranial Therapy, IEEE Trans Biomed Eng, 57: 356:368, 2010.
Stone GW, et al., Percutaneous recanalization of 19 chronically occluded coronary arteries: a consensus document: Part I, Circulation, 112:2364-2372, 2005.
Strauss BH, et al., Collagenase plaque digestion for facilitating guide wire crossing in chronic total occlusions, Circulation 108:1259-1262, 2003.
Strauss BH, et al., Collagenase Total Occlusion-1 (CTO-1) Trial A Phase I, Dose-Escalation, Safety Study, Circulation, 125:522-528, 2012.
Suero JA, et al., Procedural outcomes and long-term survival among patients undergoing percutaneous coronary intervention of a chronic total occlusion in native coronary arteries: a 20-year experience, J American College of Cardiology 38:409-414, 2001.
Thind A, et al., The Use of US Stimulated MBs as an Adjuvant for Collagenase Therapy in Chronic Total Occlusion, Eurointervention, 10:484-493, 2014.
Werner GS, et al., Contemporary success and complication rates of percutaneous coronary intervention for chronic total coronary occlusions: results from the ALKK quality control registry of 2006, EuroIntervention, 6:361-366, 2010.
Wijeysundera HC, et al., Relationship between initial treatment strategy and quality of life in patients with coronary chronic total occlusions. EuroIntervention, 9:1165-1172, 2014.

* cited by examiner

SYSTEMS AND METHODS FOR TREATING VASCULAR OCCLUSIONS WITH CATHETER BASED ULTRASOUND

CROSS-REFERENCE TO RELATED APPLICATIONS

This application claims the benefit of U.S. Provisional Patent Application Ser. No. 62/741,259, filed on Oct. 4, 2018, and entitled "SYSTEMS AND METHODS FOR TREATING VASCULAR OCCLUSIONS WITH CATHETER BASED ULTRASOUND," which is herein incorporated by reference in its entirety.

BACKGROUND

Cardiovascular disease (CVD) causes 31% of all deaths, globally. Heart disease and stroke continue to be the leading cause of hospitalization in the world, impacting a growing number of patients and associated with increasing economic impact. Thrombo-occlusive conditions are a significant component of this burden. Prominent examples of this are myocardial infarctions (coronary arteries), stroke (cerebral arteries), deep venous thrombosis (DVT-femoral veins), and pulmonary embolism (PE). A wide range of methods have been developed to treat blood clots generally involving medical therapy or catheter-based approaches. However, in many circumstances the effective resolution of blood clots in large vessels remains a significant clinical challenge.

Catheter-based approaches include aspiration and other mechanical retrieval devices. Aspiration devices (e.g., those manufactured by Penumbra, Inc.) can apply intermittent suction through the catheter lumen, frequently in combination with a clot "separator" device that is wire-like with a shaped tip that exits the distal end of the lumen to penetrate the clot to break it up and pull portions towards the catheter tip. Another type employs high velocity liquid jets contained within the catheter that utilize the Bernoulli Effect to capture, fragment, and remove the clots (e.g., Angiojet devices manufactured by Boston Scientific). These can involve first penetrating into the clot, releasing thrombolytic enzymes, waiting, then re-entering the clot to perform mechanical retrieval. Side holes near the distal tip permit clot fragment entry, driven by the Bernoulli Effect and the clot fragments are then removed with the return liquid flow. Another example employs a rotating screw-like mechanism within the catheter tip, which both creates suction through a side hole and mechanically fragments and removes clot material.

Catheter-based ultrasound approaches have also been described and developed for thrombolysis. Ekosonic catheters employ a series of cylindrical transducers along the distal portion of a catheter, along with side ports to release thrombolytic agents. In a clinical context, such as PE treatment, the catheter is inserted into the clot, thrombolytic agents are released and the ultrasound is turned on. The radiation pattern of the transducers that is exploited extends radially outwards from the catheter. Examples of the use of this catheter in combination with microbubble contrast agents have also been reported, where the bubbles are also introduced through the exit holes of the catheter.

Also, in an earlier stage of development, a forward looking catheter for thrombolysis has been reported. This employs a layered transducer fabrication approach, stimulating the transducer in a "lateral" mode to overcome electrical impedance matching issues, along with spherical focusing. Benchtop examples of its use with microbubbles to break up thrombus were reported. With all catheter-based approaches, there are considerations of size (i.e., diameter, stiffness, and its impact on the ability to safely enter into relevant vessels), safety (e.g., the approach, amount of thrombolytic agents, possible hemolysis), treatment duration, treatment efficacy, and cost. Smaller devices (and those with more compliant tips) will enable penetration into smaller vessels (i.e., smaller vessels in adults, or pediatric applications). Methods that can safely accelerate treatments can be advantageous to reducing treatment times (impacts cost and patient safety) and in more effectively treating the clots (e.g., larger/longer clots).

Another important class of vascular occlusions are chronic total occlusions (CTOs) of the coronary and peripheral vasculature, which are defined as vessels with blockages that result in absent blood flow for more than 3 months. CTOs begin as soft thrombotic occlusions that, with age, develop complex morphologies that include the presence of proximal fibrous caps (PFC) that are invested with stiff densely packed collagen. CTOs are frequently detected on diagnostic coronary angiograms, with incidence rates in the range of 20 percent in patients with clinically significant coronary artery disease.

While the past two decades have seen the widespread adoption of percutaneous coronary interventions (PCI) in treating acute myocardial infarctions and in the deployment of drug eluting stents, their use in CTO revascularization has been limited. This is despite there being clear evidence that successful CTO revascularization leads to improvements in cardiac function, quality of life, and long-term survival. In one previous study, for example, 64 percent of patients with a diagnosed CTO were subjected to medical treatment, 26 percent underwent bypass surgery, and only 10 percent were referred for PCI based CTO revascularization. The limited adoption of PCIs is primarily attributed to the technical difficulties associated with many crossings, which holds revascularization success rates to the 55-80 percent range. The high failure rates for attempted CTO PCI procedures are mainly due to an inability to advance a guide wire across the mechanical barrier presented by the proximal portion of the CTO, which is sometimes referred to as the PFC. As used herein, the term PFC can indicate the proximal region of a CTO, and may include deeper regions not immediately at the interface of a CTO. Newer techniques and innovations to overcome this limitation are a high clinical priority.

A promising new method to increase CTO PCI success rates is to use injections of the enzyme collagenase to degrade the mechanical integrity of PFCs. A Phase 1 clinical trial showed a 75 percent crossing rate in CTOs (median length 18 mm) that had previously failed crossings. This approach is now undergoing a Phase 2 clinical trial (TOSCA-5) for treating CTOs, where the proximal portion of the CTO is exposed to a catheter-based injection of collagenase. After a 24 hour waiting period, a second PCI is performed wherein flow restoration is attempted. While these improvements in crossing success rates in difficult lesions are encouraging, widespread adoption of this approach may involve reducing the duration of the procedure, which in some cases is performed on two consecutive days, increasing patient risk and hospital costs.

The adoption of an approach that improves crossing rates of complex lesions would not only impact the 10 percent of CAD patients that currently undergo CTO-PCI but could double the number of procedures, improving the health, quality of life and possibly longevity of a significant number of patients. In addition to coronary CTOs, there may be CTOs present in other arteries, including but not limited to the femoral artery. Further, in addition to CTOs, thrombotic occlusions are a major cause of mortality and morbidity in settings such as stroke, deep vein thrombosis, and myocardial infarction. The treatment of such occlusions at present suffers limitations and may also benefit from the development of new methods to resolve the occlusions more completely and or in a more rapid manner. There remains a need to improve the revascularization success rates of occluded large vessels in a number of clinical circumstances and to decrease procedure time.

SUMMARY OF THE DISCLOSURE

The present disclosure addresses the aforementioned drawbacks by providing a system for treating vascular occlusions. The systems includes a catheter extending from a proximal end to a distal end along a longitudinal axis and having a lumen extending therethrough. An ultrasound transducer is coupled to the distal end of the catheter and is coaxial with the longitudinal axis of the catheter. The ultrasound transducer is a cylindrical annular transducer having a lumen extending therethrough. The ultrasound transducer is configured to generate ultrasound in a forward facing direction extending outward from the distal end of the catheter.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

BRIEF DESCRIPTION OF THE DRAWINGS

FIG. 6A shows length mode pressure distributions for transducer element lengths of 6, 4.5, 3, and 1.5 mm. FIG. 6B shows pressure distributions for 6, 4.5, 3. And 1.5 mm transducer element lengths excited at a higher frequency mode than in FIG. 6A. FIG. 6C shows pressure distributions for a 2.5 mm length transducer element excited at different frequencies, which shows the difference in pressure distributions.

FIG. 8A shows pressure measurements t different driving voltages, which indicates pressure as a function of distance from space. FIG. 8B shows a relative pressure distribution map.

FIG. 9A shows pressure measured at 0.5 mm from transducer ends along center line, as a function of applied voltage for 1.5 (0.45 MHz) and 3 mm (1.2 MHz) length transducers. Mechanical breakdown occurs at high voltages for the 3 mm element. Cavitation occurs in the 3 mm transducer (lower frequency) at lower voltages. FIG. 9B shows hydrophone evidence of cavitation signal in the 3 mm transducer.

DETAILED DESCRIPTION

Figure 1:
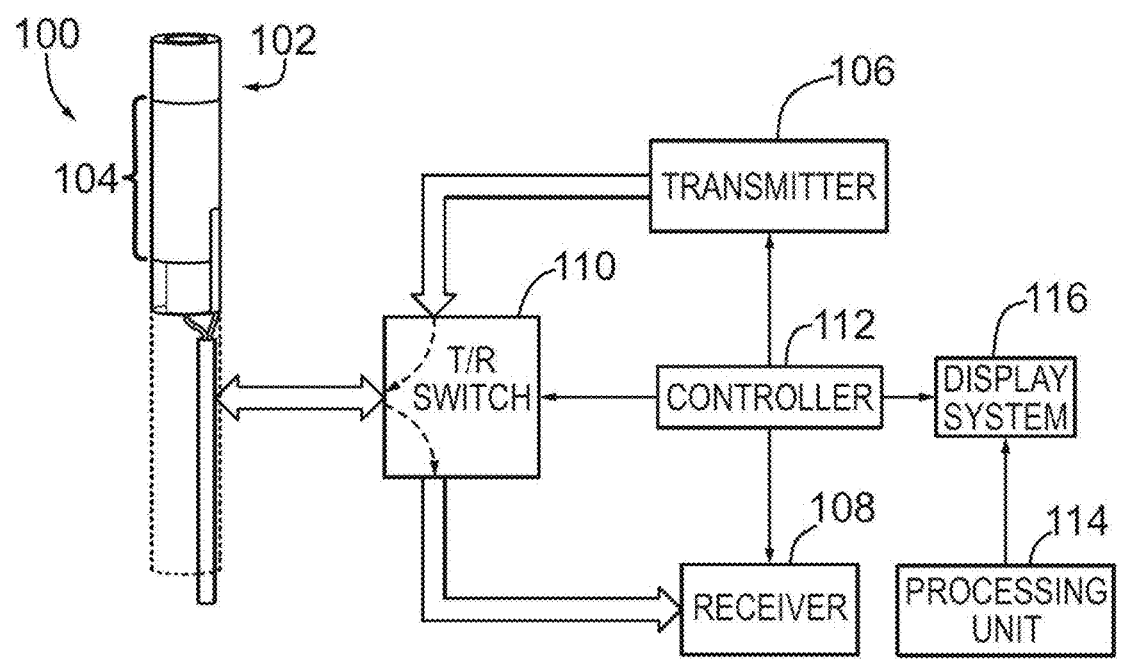
FIG. 1 is a diagram of an example of an ultrasound system that can implement the methods described in the present disclosure.

A system and method is provided for generating ultrasound at the tip of an intravascular catheter. These systems and methods may be used for the treatment of vascular occlusions, including chronic total occlusions (CTOs) and other thrombotic occlusions (e.g., deep vein thrombosis, stroke, pulmonary emboli, myocardial infarction), atherosclerotic plaques, or other tissue types. For instance, the systems and methods may be used to induce cavitation to enhance the enzymatic degradation of a vascular occlusion.

In some configurations, the approach employs a hollow cylindrical transducer that is electrically stimulated in the radial direction at a frequency or frequencies that result in therapeutically relevant ultrasound both within and forward from the catheter tip. These systems and methods can overcome electrical impedance issues for the generation of low frequencies with a smaller diameter transducer capable of negotiating into blood vessels, including arteries (e.g., coronary artery, cerebral arteries, and pulmonary arteries), veins, or both.

The hole (e.g., central lumen of a cylindrical annular transducer) within the transducer may accommodate a guidewire to facilitate its placement adjacent to the proximal portion of the occlusion. The hole will also permit cavitation agents (e.g., microbubbles), seeds, nuclei, or precursors (e.g., liquid phase perfluorocarbon droplets); lytic enzymes (e.g., collagenase, urokinase, tissue plasminogen activator ("tPA")); and/or or other therapeutic or contrast agents may be introduced through the hole and ultrasound exposures may be carried out. The hole can also accommodate the arrangement of other devices, such as a fiber optic device for optical imaging or another ultrasound transducer (e.g., a diagnostic ultrasound transducer) for ultrasound imaging.

The range of oscillation modes with such a transducer geometry can also offer control over different ultrasound field distributions at different frequencies that may be advantageous for therapeutic purposes. Ultrasound and cavitation (with or without exogenously introduced cavitation seeds or bubbles), possibly in combination with enzymes, can enhance treatment of vascular occlusions, such as in the mechanical degradation, erosion, or break-up of CTOs or thrombotic occlusions. Methods of injections and exposures include other embodiments of the present disclosure.

In one configuration, an intended application is the treatment of vascular occlusions, which may include CTOs of the coronary arteries. The systems and methods described in the present disclosure may accelerate the activity of therapeutic agents to mechanically soften CTOs or other thrombotic occlusions. Therapeutic agents may include enzymes (e.g., collagenase, tPA, urokinase), thrombolytic drugs, and so on. Enzymes such as collagenase can be useful for treating CTOs, and enzymes such as tPA or urokinase can be useful for treating thrombotic occlusions. One approach may include exposing the proximal region of a CTO or other thrombotic occlusion with a catheter based administration of a therapeutic agent, and then attempting revascularization on a subsequent or following day to permit sufficient time for the softening to occur. This approach uses two separate percutaneous interventions, and the associated costs and logistical/scheduling requirements. Alternatively, the method described below may reduce this to a single session, which would reduce time and costs. This latter approach may also facilitate widespread adoption, thereby having the potential to impact the treatment of a large group of cardiac.

It is contemplated that in some instances the combination of ultrasound with cavitation can be sufficient to achieve therapeutically relevant effects without the need for administering a therapeutic agent. Further, it is possible for the ultrasound on its own (e.g., without the introduction of cavitation seeds such as preformed microbubbles, droplets, and so on) to be capable of initiating therapeutically relevant cavitation that will degrade the occlusions. In the case of a thrombotic occlusion, where the catheter may achieve therapeutic effects more rapidly, thereby resulting in an erosion of the proximal end of the occlusion, successive advances (e.g., downstream movements to compensate for the erosion) of the catheter and treatments may be made to enable the removal of the entire occlusion.

A catheter based deployment may allow for such approaches to be a viable clinical option in the context of an interventional cardiology suite. This is for at least the following reasons. The systems and methods described in the present disclosure enable controlled delivery of ultrasound to a specific region of a coronary artery in a beating heart. The systems and methods described in the present disclosure implement a catheter that can already be in place for the potentiation of the activity of enzymes. The simplicity of using a single catheter for the delivery of both a therapeutic agent and ultrasound would remove a central adoption barrier.

A catheter based deployment may allow for such approaches to be a viable clinical option in the context of interventional radiology (e.g., in the setting of pulmonary embolism) or other clinical applications (e.g., deep venous thrombosis, or in pediatric thrombotic occlusions). For instance, the systems and methods described in the present disclosure enable controlled delivery of ultrasound to a specific region, such as to a specific region of a cerebral artery. The systems and methods described in the present disclosure also implement a catheter that can already be in place for the potentiation of the activity of thrombolytic enzymes or drugs. The simplicity of using a single catheter for the delivery of both enzymes and ultrasound can remove a central adoption barrier.

A catheter based deployment may allow for such approaches to be a viable clinical option in the context of interventional neurology (e.g., in the setting of a stroke) or other clinical applications. For instance, the systems and methods described in the present disclosure enable controlled delivery of ultrasound to a specific region, such as to a specific region of a cerebral artery. The systems and methods described in the present disclosure also implement a catheter that can already be in place for the potentiation of the activity of enzymes. The simplicity of using a single catheter for the delivery of both enzymes and ultrasound can remove a central adoption barrier.

A catheter based deployment may allow for such approaches to be a viable clinical option in the context of interventional radiology (e.g., in the setting of pulmonary embolism) or other clinical applications (e.g., deep venous thrombosis, or in pediatric thrombotic occlusions). For instance, the systems and methods described in the present disclosure enable controlled delivery of ultrasound to a specific region, such as to a specific region of a pulmonary cerebral artery.

In one configuration, a catheter device and methodology for using ultrasound in combination with therapeutic agents (e.g., enzymes) to accelerate the softening of CTOs (e.g., with collagenase) or other thrombotic occlusions (e.g., with tPA or urokinase) is provided. A catheter may be designed to first have an outer diameter at the tip on the order of 1-2 mm or less to permit its introduction into the coronary vascular tree. The outer diameter may also be larger, in the case of larger blood vessels (e.g., pulmonary or femoral arteries). Second, the tip may be hollow to accommodate the introduction of guide wires to direct the tip to be adjacent to a treatment region, such as adjacent the CTO PCF. Such guide wires may be on the order of 0.4 mm in diameter, but may also be larger or smaller than 0.4 mm. There may therefore be a lumen along the length of the catheter, extending through the tip, and this lumen may also be present to enable the introduction of therapeutic agents and microbubbles (or other cavitation seeds, cavitation nuclei, or cavitation precursors). A plurality of other lumens may also be present, for guide wires, injections, aspiration, or to accommodate electrical connections to the transducer(s).

The ultrasound transducer is configured such that the ultrasound beam is at least partially projected forwards from the tip. The ultrasound transducer may also be configured to generate ultrasound of frequencies and amplitudes that are capable of inducing therapeutically relevant oscillation amplitudes of cavitating (e.g., inducing oscillations, disruption, or translating of motion) bubbles. As one example, the frequencies can be on the order of 1-5 MHz or below, though frequencies of up to 20 MHz and as low as 20 kHz are also contemplated. The configuration of the ultrasound transducers described in the present disclosure provide advantages over disc transducers of similar size (e.g., diameter of several millimeters or below) operating in a "thickness" mode at similar frequencies and with a similarly sized hole (e.g., a 0.4 mm hole) drilled therein. Such disc transducer will have an electrical impedance such that very poor efficiency in terms of stimulating vibrations would be achieved, thus limiting the achievable pressure levels. This is contrary to the ultrasound transducers described in the present disclosure, which enable higher efficiency and with a broader range of achievable pressure levels.

In some configurations, a hollow cylinder transducer may be used, which is polarized radially between electrodes located on their inner and outer cylindrical surfaces. Example configurations of hollow ultrasound transducers are described in U.S. Pat. No. 9,387,515, which is herein incorporated by reference in its entirety. Electrical impedance limitations may be overcome such that lower frequencies can be used more effectively (e.g., at higher amplitudes). Here, the electrical impedance is a function of the (larger) inner and outer surfaces and, thus, it provides a way to lower the impedance to enable smaller dimension emitters. The hollow core can accommodate a guidewire to position the tip and may also provide a conduit through which the local delivery of cavitation seeds (e.g., bubbles) and lytic enzymes can be achieved.

When electrically stimulating such a transducer, different vibration modes (e.g., length mode, radial thickness mode, and radial/circumferential mode) can result depending on the transducer material and dimensions (e.g., inner radius, outer radius, length). The length mode, or extensional mode, preferentially excites along the length mode axis. An extensional mode (e.g., emitting substantially at the transducer ends) may be stimulated when radially applied voltages are at the extensional resonant frequency, which decreases with increasing length. The thickness mode resonance depends largely on the difference between the inner and outer radii, and creates both inward and outward radially propagating waves. The circumferential mode largely involves modulations of the circumference. With all these modes, ultrasound waves or other energy are projected in different directions (e.g., internally, radially outwards, outwards from the ends) to different degrees. These patterns can be complex and are generally frequency dependent. There may also be harmonics of these resonances present. Depending on the relative values of the length, inner and outer radii (and the material), there may be not be distinct resonances present, yet substantial emissions may occur that are therapeutically relevant Such a transducer may be situated at the tip of a catheter and operated in different modes to project significant MHz to sub-MHz range ultrasound in a forward-facing direction. It is recognized that each vibration mode may emit ultrasound in different directions (i.e., not exclusively in one direction). It is also recognized that combinations of modes may be present and that operating the transducer in such a manner may be advantageous. Following existing procedures for collagenase based CTO therapy, the catheters described in the present disclosure may be slid into place adjacent to or slightly within a PCF over a guide wire. The wire may be extracted, and a series of microbubble injections/exposures may occur. This may then be followed by injecting collagenase or another enzyme. After a waiting time within the PCI session, a crossing attempt may be made. Alternatively, there may be a second PCT session on the same day or on another day.

Catheter-based cylindrical transducers have been reported previously, but are intended to project ultrasound energy radially outwards in a manner that is compatible with treating atherosclerotic plaques, or if pushed into soft blood clots, but this not compatible with treating CTOs, which are mechanically stiff and generally do not permit entry, or some thromboses. It may also be advantageous to not push the catheter into some soft thrombotic occlusions. A hollow transducer that can transmit ultrasound in a forward facing direction is advantageous because it may also accommodate a guidewire to locate within a narrow lumen and allow for filling with cavitation seeds (e.g., bubbles) and/or therapeutic agents (e.g., enzymes, thrombolytic drugs) for the treatment of CTOs and thrombotic or other vascular occlusions.

The ultrasound energy that is directed forwards may be influenced by the transducer dimensions, as well as the manner in which it is mounted within the catheter. Materials and configurations that promote the direction of energy forwards may be selected based upon various engineering considerations, such as spatial constraints, rigidity, reliability, visibility, and the like. In some configurations, the device may not only include the catheter but also the transducer driving electronics (e.g., waveform generator, other associated pulsing controls, timing controls, signal amplifiers, cavitation feedback control aspects), which may be external to the subject, and controlled flow pumps to introduce cavitation seeds (e.g., microbubbles, liquid phase droplets), therapeutic agents, or both. In some configurations, the method may encompass using interleaved sequences of controlled injections and ultrasound bursts that are optimized to promote the therapeutic action of cavitation at the PFC or thrombotic occlusion.

In some configurations, a cavitation seed may be released at a catheter tip and subjected to forward looking ultrasound. Particular sequences of injection and pulsing schemes may be used to promote, through radiation forces, the accrual of relevant bubble sizes to the PFC or thrombotic occlusion region and subsequently stimulate them in a therapeutically relevant manner. This may result in not only damaging the PFC or thrombus, but also promoting the transport and action of enzymes within or adjacent to the PFC or thrombus. Different sequences of introducing enzymes (or drugs), cavitation agents, and exposing with ultrasound are considered, including having concurrent injections of cavitation agents and enzymes (or drugs).

In some configurations, the use of the transmit transducer, or the addition of a second passive transducer element, may enable cavitation detection for the purposes of treatment control feedback or monitoring. The use of these cavitation signals, either passively monitored by a single transducer, multiple transducers, or active detection (e.g., sending pulses to test for bubble presence) is an advantageous aspect of some implementations. In one configuration, PVDF or another piezoelectric material may be layered onto the surfaces of the transmit transducer. Another variation of this would be to have an additional cylindrical transducer, possibly with a different size (e.g., a different length) or a different material. In addition, the second layer or transducer, on its own or in combination with the original transducer could be used to provide information relevant to detecting the position, geometry, or therapeutically relevant status of the occlusion. This may involve, for example, sending ultrasound pulses with one or both of the transducers, receiving the signals from one or both of the transducers, acquiring the signals, and processing them in a manner that provides relevant information or data for planning, guiding, and/or monitoring the treatment process. This information may be in the form of an image. An image may, for example, be used to aid in the positioning of the catheter or to monitor occlusion erosion. The nature of the pulsing and subsequent processing of the receive signals may also be used to infer flow information. For example, appropriately timed successive pulses of particular lengths can be analyzed (e.g., by looking at decorrelation, or pulsed wave or color flow Doppler based approaches) to extract information about flow status within the vessel. This information may be derived for positions radial to the transducers, or distal to the catheter tip. This information could be relevant for assessing the relative location of the occlusion, and provide an indication of when flow is restored.

The simultaneous stimulation of both transducers can also be implemented, and may be advantageous for imaging purposes and/or to infer information about the occlusion position or properties. In such implementations, associated electrical wiring may be arranged to enter into the proximal catheter end and connect to the transducers at or near the catheter tip.

In other configurations, the transmit transducer can be used to detect cavitation for the purposes of using this as feedback to control and monitor the treatments (or formation of bubbles within the transducer). This self-sensing may be done in different ways, and may offer a reduced complexity and cost relative to having a second transducer or transducer array present.

In one non-limiting example, the current going to the transducer can be monitored, such as when cavitation is present, adjacent to or in proximity to the transducer (e.g., due to the pressure field created by the ultrasound transmission). In these instances, the cavitation will produce pressure wave emissions that will impinge upon the transducer and create electrical signals. These signals will be superimposed on the transmit signals and may be detected, for example, as fluctuations in the current (i.e., part of the current will be associated with the driving voltage, and part with the signals associated with the driving signals). The cavitation signals may be separated based on different characteristics, such as frequency content. In these implementations, there may also be spatial information in the signals (e.g., due to diffraction patterns and the sensitivity of different oscillation modes). Collectively, these signals and their interpretation based on the system design can be used to infer relevant information about the degree and possibly spatial distribution of cavitation. This can be advantageous when used for controlling the system, Variations of the transmit signal (e.g., frequency, amplitude) may be used to assist in the interpretations of these signals.

Additionally or alternatively to impinging cavitation signals giving rise to additional signals (e.g., current variations), the effect acoustic impedance at the boundary or adjacent to the transducer will also be affected. This in turn can affect current signals. Additionally, it may also affect the resonance behavior and effective electrical impedance of the transducer in ways that can be detected (e.g., through impedance measurements, recognizing that a transmit pulse can be shut off transiently to permit such a measurement; or for example sending a "probe pulse" and measuring its response).

In other configurations, cavitation signals arising from the catheter tip stimulation can be monitored by hydrophone arrays (e.g., sparse arrays) or single transducers situated on the skin surface. Signals from these arrays would then be incorporated into the system and be used for monitoring or controlling the treatments.

In addition to conventional microbubble agents, other cavitation seeds may be used. Microbubbles are typically encapsulated (e.g., phospholipid shells that are pegylated) bubbles containing high molecular weight gases, and can typically range in diameter from approximately 200 nm or below up to 10-20 microns. The formulations may be polydisperse (i.e., wide size ranges) or be manipulated or manufactured to have more narrow size populations. In one non-limiting example, nanometer scale agents (e.g., 10-1000 nm) containing small amounts of gas may be used and such agents may permeate the PFC or thrombus such that when sonication occurs this will induce CTO or thrombus damage that may provide a therapeutic effect.

Bubbles smaller than 1 micron are sometimes referred to as "nanobubbles"; as used herein, the term "microbubbles" more broadly includes the potential use of nanobubbles. As used herein, the terms cavitation "seed" or "nuclei" are used to broadly refer to particles such as preformed bubbles (referred to above), or for example "nanocups" or other discrete particles that typically, but do not necessarily, contain gas. When such cavitation seeds are subjected to ultrasound of a certain frequency (or frequencies, or complex linear or nonlinear waveform) the associated gas and/or vapor filled body can oscillate, potentially grow, rapidly expand, collapse, translate, and exhibit other behaviors. Such behaviors can create mechanical (e.g., displacement, streaming, other), chemical, thermal, and other effects that can be relevant to promoting or facilitating the degradation and/or removal of vascular occlusion (e.g., thrombus, chronic total occlusions, atherosclerotic plaques, or other tissue types) on their own or in combination with enzymes or drugs and/or other mechanical devices.

Cavitation seeds may also take the form of liquid phase droplets, which can be converted by ultrasound to a gas or vapor filled bodies (e.g., bubbles) that can then be further stimulated by ultrasound to behave in a therapeutically beneficial manner. These droplets may also be coated, for example by phospholipids and pegylation molecules to promote stability both in droplet form, and also once converted to bubbles. These can also be referred to here as cavitation "precursors". Such cavitation seeds and precursors may confer advantages such as being resistant to possible overpressure effects arising from the injection procedures or from not being subject to flotation effects giving rise to heterogeneous media once reaching the catheter tip. The system can also be used to induce cavitation in the absence of explicitly introducing exogenous cavitation seeds (e.g., microbubbles) or precursors. In these instances, the cavitation may be introduced in whatever fluid is present within the catheter (e.g., saline, diluted therapeutic agent). There may or may not be a degree of small bubbles present in such solutions. Preformed microbubbles, liquid phase droplets, and other acoustically active particles (e.g., nanocups) can be referred to as ultrasound "contrast agents".

Further, when operating without cavitation seeds (intentionally introduced), having a stabilizing compound within the fluid (e.g., albumin, phospholipids) may result in the formation of bubbles that are stabilized by encapsulation with the compounds. This, in turn, may promote stability of the resulting bubbles that may be advantageous when they are subsequently positioned adjacent to the occlusion. The production of more stable bubbles in this context may be facilitated by having dissolved gases (e.g., high molecular weight perfluorocarbons) present in the solution. Effectively, this method of bubble production can be done with so-called "acoustic horns", though there can also be present a gas layer above a liquid layer in this context. The cavitation seeds may also contain or be associated with a therapeutic agent, such as collagenase or other thrombolytic enzymes or drugs.

In some examples, the ultrasound transducer can be used to convert precursors to bubbles, such that these are then employed to treat occlusions. In some configurations, cavitation seeds (e.g., existing bubble populations) can be modified to have a distribution that is more favorable for therapy.

Additionally or alternatively, bubbles can be created with the transducer, and whatever is present in the solution may or may not act to stabilize the bubbles, and these bubbles will then be used to treat vascular occlusions. In these configurations, the cavitation can be produced primarily, but not necessarily exclusively, within the hollow portion of the transducer. In still other examples, cavitation can be induced by the transducer in the absence of externally introduced cavitation seeds, but rather in the occlusion itself. This may occur within the transducer hollow, or distal to its tip. Occlusion material may be present in these locations by situating the transducer adjacent to the occlusion, and possibly by applying pressure along the catheter axis and/or by applying suction or using wire based devices (e.g., "separator" for thrombus).

In some configurations, contrast agents may include liquid droplets or other cavitation seeds, where there may be a bi-modal stimulation of the transducer: for example, first pulsing at the radial thickness resonant frequency (e.g., with a selected voltage amplitude) to cause inward propagating wave within the transducer to convert the seeds to gas bodies, then to switch to a more forward looking ultrasound mode (e.g., frequency and amplitude) to achieve therapeutic effects. The liquid droplets can be converted to gas bubbles within the cylinder by switching its operating frequency such that the ultrasound waves activate within the tube first, and then switch back to a frequency that favors the forward looking propagation of ultrasound where the resulting bubbles can act in a therapeutic manner at the occlusion. It is recognized that all frequencies (associated with a particular transducer resonant mode or not) will result in a degree of ultrasound propagation within the hollow portion of the transducer. Therefore, any frequency or combination of frequencies may be in principle used to achieve the phase conversion effects.

In some configurations, there may be an ultrasound wave present within the transducer body (e.g., the hollow portion). Such a wave may have a different pressure amplitude than the outwardly propagating ultrasound. Sequences of injection and ultrasound stimulation (e.g., frequency selection in combination with transducer design) may be used such that the effects of this wave will not detrimentally affect the agent's therapeutic capacity as it exits the distal tip.

In some configurations, very large bubbles that may occupy close to or the full inner lumen of the transducer can be employed. These may be introduced individually into the transducer and converted into smaller, therapeutically relevant bubbles by certain oscillation modes of the transducer. This procedure would involve the controlled introduction of bubbles towards the proximal end of the catheter, possibly with a separate entry point. The gas could be, for example perfluorocarbon, oxygen, medical air, or other types, and the liquid surrounding the bubble could contain stabilizing agents (e.g., albumin, phospholipids). For this, the controlled conversion and detection of the bubble location, for example with specific detection pulses sent to the transducer and received, would be advantageous.

In some configurations, intentionally stimulating inwardly propagating waves in combination with modes (or at frequencies) with forward projected ultrasound may be advantageous. In one non-limiting example, stimulating a radial thickness mode at a frequency corresponding to the radial thickness resonance frequencies (~5-15 MHz, for example) may result in a pronounced wave in the center of the tube.

By selecting the transducer dimensions such that the inner diameter corresponds to the wavelength of the resonant frequency (or odd multiples thereof) of the radial thickness mode there will be an amplified pressure peak on axis within the tube due to constructive interference. Though higher frequencies do not favor cavitation within liquids, they may be advantageous for converting liquid phase droplets to gas phase bubbles, which may occur more readily at higher frequencies, and which can subsequently be stimulated at lower frequencies (e.g., with extensional mode ultrasound) as they exit the transducer tip. Although the radial thickness mode is mentioned as an example for this application, it is recognized that other modes, or frequencies that are not associated with any mode, may achieve the above effects of conversion. Radiation forces may be used at different times in this process, both outwardly and inwardly directed. The length and circumferential modes may also be used for this purpose, according to the desired amplitude, frequency, and spatial distribution of the ultrasound field within the tube. It is recognized that the ultrasound field can be highly sensitive to these parameters.

In one non-limiting example, it was shown in an animal model of CTO using transcutaneous ultrasound and microbubbles that the system and method of the current disclosure accelerates the PFC softening process, due to microbubbles damaging the PFC surface.

The systems and methods described in the present disclosure can also incorporate aspiration functionality. Catheter based vacuum/suction aspiration approaches are currently employed to assist in the removal of blood clots. The central hollow channel in the transducer can act as a conduit to implement an aspiration approach (i.e., a path through which occlusion material could exit). The central hollow channel can also accommodate wires and devices that are used to extend past the catheter tip to enter into thrombus to assist in breaking it up or pulling it backwards to be close to or within the catheter tip, at which point aspiration can transport the clot along the catheter lumen and exit the body. Associated elements (e.g., suction, perhaps intermittent, control; or suction and ultrasound) would then be added to the external aspect of the device. The combined use of ultrasound, cavitation (with or without cavitation seeds), and possibly therapeutic agents (e.g., enzymes) may be advantageous in accelerating or improving the effectiveness of aspiration based methods.

An example of this approach without the use of externally introduced cavitation seeds or thrombolytic enzymes is as follows. The catheter tip can be placed near or in contact with the thrombus, for example under fluoroscopy guidance and possibly with the use of a guide wire. Cavitation can then be initiated with the transducer. The purpose of the cavitation is to mechanically degrade the thrombus such that it can be removed through the catheter through suction, possibly with the assistance of a retrieval device (e.g., "separator") as described above. Ultrasound frequencies and transducer oscillation modes that produced cavitation in front of the tip, at the tip, and within the tip can be implemented. The transducer stimulation can be repetitive pulsing at a single frequency, or can use different frequencies during the course of treatments, such that spatially different regions of the clot are degraded. Cavitation within the tube may facilitate the degradation of the clot such that aspiration is more readily achieved in that the degraded thrombus material will present less resistance. The treatment of an occluding clot may then include a series of steps, beginning at the proximal end, whereby the above steps are repeated to progressively remove the clot.

An alternate implementation of these methods combined with aspiration can entail having a secondary channel with an entrance towards the device tip, through which the occlusion material could be transited outside the body though the length of the catheter FIG. 1 illustrates an example of an ultrasound system 100 that can implement the methods described in the present disclosure. The ultrasound system 100 includes a catheter-based transducer array 102 that includes a plurality of separately driven transducer elements 104. The transducer array 102 can include any suitable ultrasound transducer array, including a hollow cylinder transducer. Similarly, the transducer array 102 may in some instances include or otherwise be configured as a 1D transducer, a 1.5D transducer, a 1.75D transducer, a 2D transducer, a 3D transducer, and so on.

When energized by a transmitter 106, a given transducer element 104 produces a burst of ultrasonic energy. In some configurations, the ultrasonic energy reflected back to the transducer array 102 (e.g., an echo) can be converted to an electrical signal (e.g., an echo signal) by each transducer element 104 and can be applied separately to a receiver 108 through a set of switches 110. The transmitter 106, receiver 108, and switches 110 are operated under the control of a controller 112, which may include one or more processors. As one example, the controller 112 can include a computer system. In some configurations, the ultrasound system 100 may operate in a transmit-only capacity, such that the ultrasound system 100 may not need a receiver 108.

The transmitter 106 can be programmed to transmit unfocused or focused ultrasound waves. In some configurations, the transmitter 106 can also be programmed to transmit diverged waves, spherical waves, cylindrical waves, plane waves, or combinations thereof. Furthermore, the transmitter 106 can be programmed to transmit spatially or temporally encoded pulses.

When present, the receiver 108 can be programmed to implement a suitable detection sequence for imaging or otherwise measuring the environment surrounding the catheter. In some embodiments, the detection sequence can include one or more of line-by-line scanning, compounding plane wave imaging, synthetic aperture imaging, and compounding diverging beam imaging.

In some configurations, the transmitter 106 and the receiver 108 can be programmed to implement a high frame rate. For instance, a frame rate associated with an acquisition pulse repetition frequency ("PRF") of at least 100 Hz can be implemented. In some configurations, the ultrasound system 100 can sample and store at least one hundred ensembles of echo signals in the temporal direction.

The controller 112 can be programmed to design an imaging and microbubble stimulating sequence using the techniques described in the present disclosure, or as otherwise known in the art. In some embodiments, the controller 112 receives user inputs defining various factors used in the design of the imaging sequence.

A scan can be performed by setting the switches 110 to their transmit position, thereby directing the transmitter 106 to be turned on momentarily to energize transducer elements 104 during a single transmission event according to the designed imaging and microbubble stimulating sequence. The switches 110 can then be set to their receive position and the subsequent echo signals produced by the transducer elements 104 in response to one or more detected echoes are measured and applied to the receiver 108. The separate echo signals from the transducer elements 104 can be combined in the receiver 108 to produce a single echo signal.

The echo signals are communicated to a processing unit 114, which may be implemented by a hardware processor and memory, to process echo signals or images generated from echo signals. As an example, the processing unit 114 can image a CTO or an anatomy if interest and stimulate a microbubble or other contrast agent using the methods described in the present disclosure. Images produced from the echo signals by the processing unit 114 can be displayed on a display system 116.

Figure 2A:
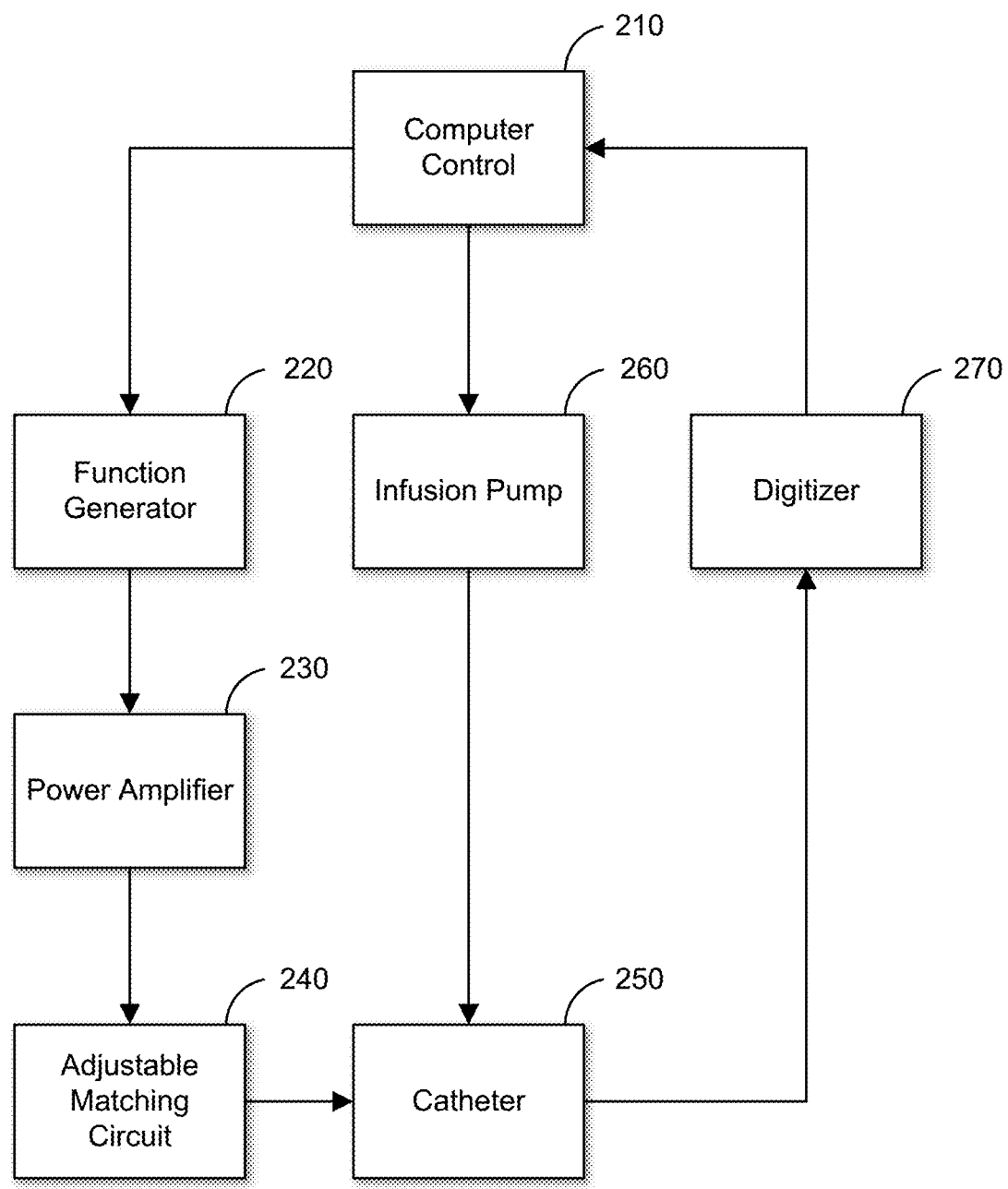
FIG. 2A is a block diagram for one configuration of the system.

Referring to FIG. 2A, a block diagram for one configuration of the system is shown. Computer control 210 (e.g., a controller, a processor) may provide for control of the exposure sequences and fluid introduction can be done on a computer or other appropriate system. Function generator 220, power amplifier 230, and adjustable or fixed impedance matching circuit 240 make up elements of the system that supply the transmit power sequences to the catheter transducer 250 (including associated electronic circuits). One or more pumps (e.g., one or more infusion pumps) 260 may provide microbubble injection for catheter 250, or provide for introduction of other fluids. Digitizer 270 may detect received signals from cavitation. Also present but not shown are the 'patient interface module' connecting the external system to the proximal catheter tip. A pumping system may enable the introduction of relevant fluids, and sequences of fluids. In some implementations, the pumping system can include more than one pump that are each controlled by the system such that there can be independent control of two or more of flush, contrast, cavitation seeds, and/or enzymes (or drugs). In an alternative to use of the pumping system, manual introduction of relevant fluids is also possible directly into the catheter. The guidewire may be inserted manually.

The proximal tip of the catheter may permit electrical connections, guidewires, and the introduction of fluids relevant to the procedure. The main shaft of the catheter may have one or more hollow portions. Fluids can include flushing fluids (e.g. saline), contrast (e.g. radiopaque for imaging), suspensions of cavitation seeds (e.g. encapsulated microbubbles) and therapeutic agents (e.g. lytic agents such as collagenase, tissue plasminogen activator, urokinase).

Figure 2B:
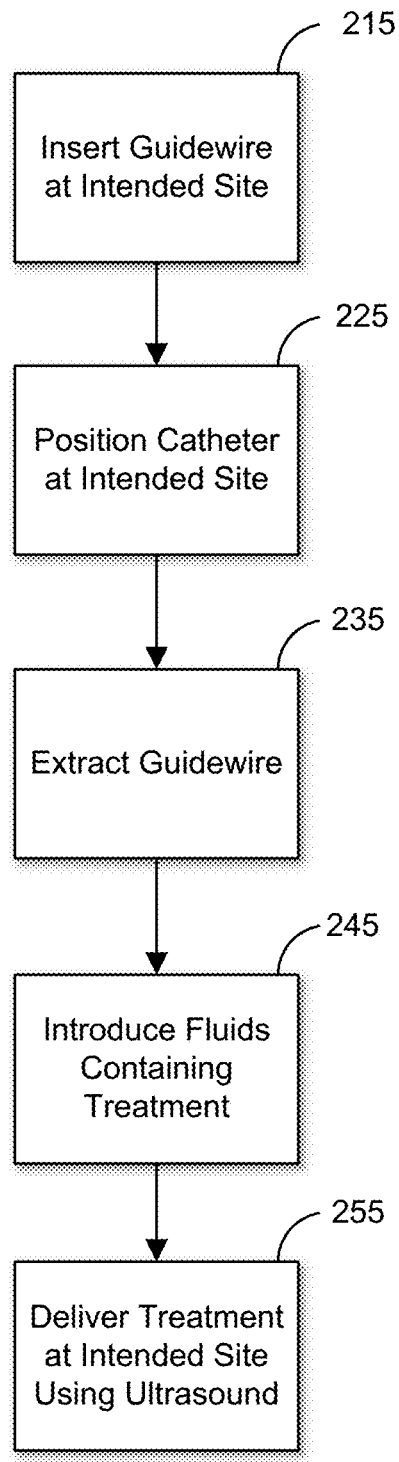
FIG. 2B is a flow chart for one non-limiting example of the method of the present disclosure.

Referring to FIG. 2B, a flow chart is shown for one non-limiting example of the method of the present disclosure. A guidewire is inserted at the intended site at step 215, such as at the site of an occlusion. A catheter is positioned at the intended site at step 225, where the site may have been identified by ultrasound imaging. The guidewire may be extracted at step 235. Fluids are introduced at step 245, and the fluids may contain a treatment, such as a collagenase. Ultrasound is then used to ensure that the treatment is delivered at the intended site at step 255, such as by rupturing microbubbles containing the treatment at the surface of the occlusion.

In some configurations, a single hollow lumen catheter may be used where the guidewire may be extracted once the catheter is positioned at the intended site. Then fluids may be then introduced through the channel. Other configurations are also possible, such as a multi-lumen channel, or a tapered channel which will permit the partial extraction of the guidewire. It is also envisioned that after the introduction of fluids the guidewire may be re-introduced and positioned with its tip in a location in proximity to the transducer that may result in favorable ultrasound energy distribution (e.g. facilitating the forwards projection of energy).

In some configurations, the inward energy discussed above may affect cavitation agents, in either a favorable or deleterious manner (e.g., destroying bubbles). Therefore, with a view to ensuring that viable cavitation seeds are situated external to the tip, it is envisioned that controlled sequences of flow and exposures may be advantageous. For example, if an agent in the tip is destroyed by an exposure burst, then prior to the next exposure burst being applied, sufficient volume of cavitation agent (possibly with therapeutic agent) can be displaced such that viable fluids are present at the tip. Designs may also be used that minimize this effect (e.g., through inner sheath designs, choice of transducer length, thickness operating frequencies). If the effect of exposures on the cavitation agent is favorable (e.g., modifying pre-existing bubbles to a certain size or initiating cavitation from liquid phase droplets or from other cavitation seeds including those present within the administered solution) then this may be considered in the exposure-flow sequences. For example, the sequence may have a component specifically related to in-tube cavitation, followed by a fluid displacement (possibly augmented by radiation pressure) pushing the bubbles outwards, followed by a therapeutic sequence when they are adjacent to the target region.

Figure 3A:
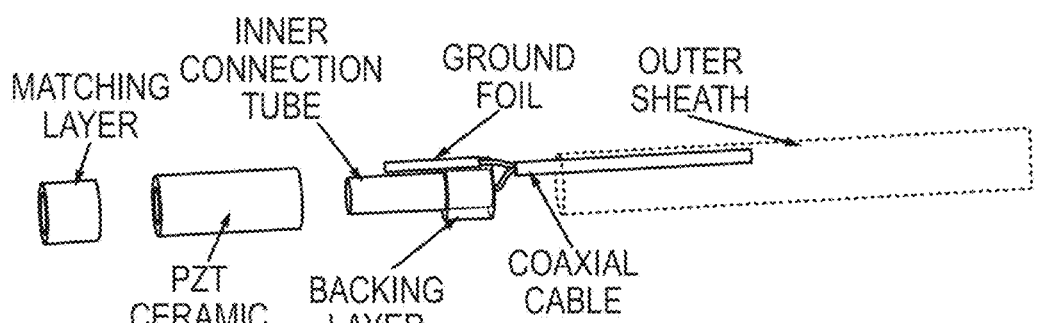
FIG. 3A is an exploded view of a schematic of an example configuration of the catheter tip.
Figure 3B:
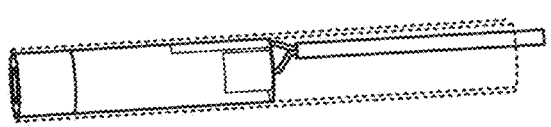
FIG. 3B is a collapsed view of one example of the catheter device.
Figure 3C:
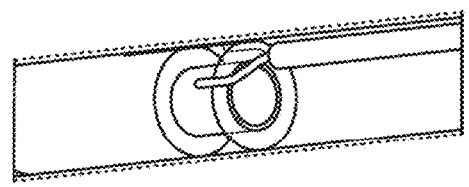
FIG. 3C is a close up view of one example of the device.

Referring to FIGS. 3A-C, non-limiting example configurations of the distal tip region of a device are shown. FIG. 3A depicts an exploded view of a schematic of an example configuration of the catheter tip. FIG. 3B depicts a collapsed view of one example of the device. FIG. 3C depicts a close up view of one example of the device showing signal wire attachment to inner connection tube and ground connection to outer foil, both insulated in the backing layer. External electrical connections that provide the driving voltage to the transducer element, pass through the catheter from an external source and connect to the transducer. This may be achieved either through contact with the inner and outer electrode surfaces (e.g., the electrical layer atop the inner and outer transducer surfaces) or, for example, through the use of conductive inner and/or outer conductive sheaths (e.g., hollow tubes or foils) that may be partially of fully in contact with the inner electrode surface of the transducer, (e.g., the example inner connection tube referenced in FIG. 3A) possibly adhered to the inner transducer surface with, for example, a suitable conductive glue or epoxy. Such a tube or sheath or coating can also fulfill the function of protecting and isolating the transducer from the guidewire or other devices that go through the transducer lumen, as well as providing electrical isolation from the patient and a biologically relevant barrier. This tube or sheath and the entire catheter may also be coated with thin layers of material that facilitate electrical and biological isolation (e.g., paralyne).

The 'backing layer', through its design and material may facilitate electrical contact between the electrodes and the external wiring system. The electrodes (e.g., evaporated or sputtered or deposited by other means) on the inner and outer surface of the transducer may be patterned in a way that permits more complex oscillation modes of the transducer. This may entail multiple electrode attachments and corresponding driving channels and the associated external electronics. For example, a series of banded (e.g., ring-like) electrodes along the length may be used and stimulated in a manner that alters the resultant internal or external (e.g., forward-looking) ultrasound field in a manner that is desirable. The electrode pattern may also be more complex, on either the inner or outer surfaces, but be connected with only a single wire on each side to reduce the complexity of implementation. The transducer tube itself, for example, on its proximal side may also have notches, or the like, formed therein in order to facilitate the positioning of and/or adherence of connecting electrode wires.

In some configurations, different transducer materials and combinations thereof may be used, and their construction may have different layers, radially or axially. There may also be a layer (e.g., additional hollow cylinder element, layer of a different material) at the distal side of the transducer, referred to in FIG. 3A as a "matching layer". One function is to provide mechanical isolation and protection for the transducer from the vessel. Another function is to facilitate a favorable energy projection (amplitude, spatial distribution). For example, it could fulfill the function of acoustic impedance matching to increase the amplitude of the ultrasound pressure field in the forwards direction. It may have a geometry departing from that depicted such that it impacts the ultrasound field in a favorable manner, for example assisting in focusing (e.g., geometrically, synthetic aperture approaches). A more complex geometry may also be present, such that for example it facilitates cavitation. There may also be a second transducer at the distal portion of the catheter, for example a PVDF layer adhered to the distal side of the first transducer in the form of an annulus, which can be used to detect "cavitation" signals induced by the first transducer. These may be used to assess therapeutic effects, or to control the treatment procedure. For example, through the amplitude of different frequency components being used to determine the applied power levels, or the duration of applied power. In this case additional electrical connections may be present along the catheter.

In some configurations, an outer sheath may cover the transducer and may extend past the tip of the transducer. The distal tip material may be constructed to facilitate effective coupling with the occlusion (e.g., CTO or thrombus) as well as to be sufficiently compliant in consideration of safety when contacting vascular tissue. A radiopaque marker, element, or portion of the sheath may be included to facilitate the ultrasound catheter's location and positioning under imaging (e.g., fluoroscopy). This marker may be situated at or near the catheter tip, and in some configurations may be situated even more proximal than the transducer assembly elements.

Figure 4:
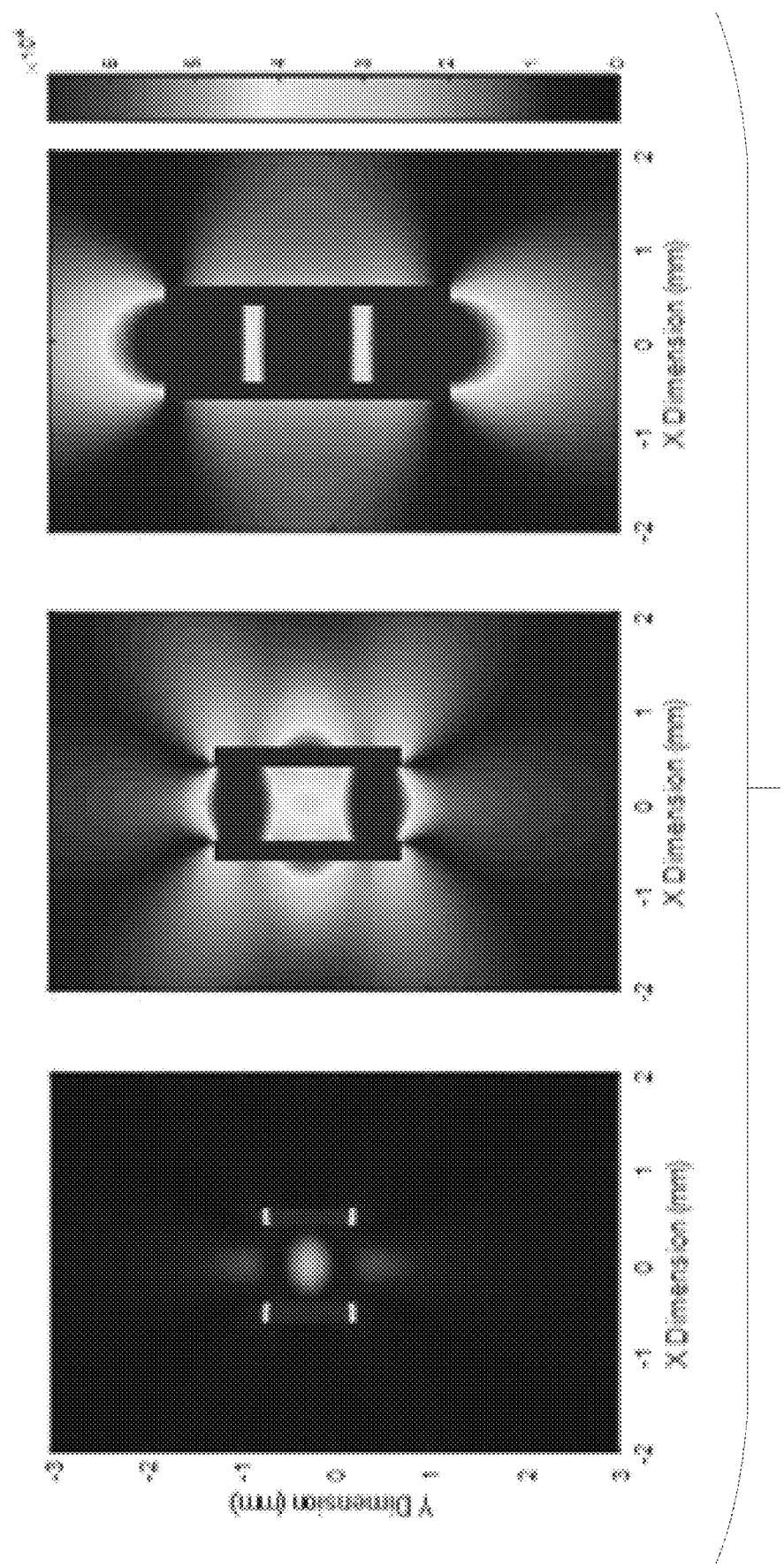
FIG. 4 is an image of non-limiting examples of finite element model simulations of pressure maps.

Referring to FIG. 4, a non-limiting example finite element model simulations of pressure maps of 1 mm, 2 mm, and 3 mm long PZT-4 ceramic cylinders simulated in PZFlex and driven at their length-mode resonance frequencies (1808, 782, and 554 KHz, respectively) is shown. For display purposes, the amplitudes have been saturated in some areas. It is recognized that the materials and geometries of all elements in the tip region can affect the nature of the ultrasound field, both within the distal tip, radially outwards from the tip, and in the forward looking direction relative to the distal end of the tip. A user may therefore select the transducer material, its length, inner radius, and outer radius for optimal results. In FIG. 4, simulations show the effect of length on the ultrasound field while maintaining fixed inner and outer radii.

Figure 5:
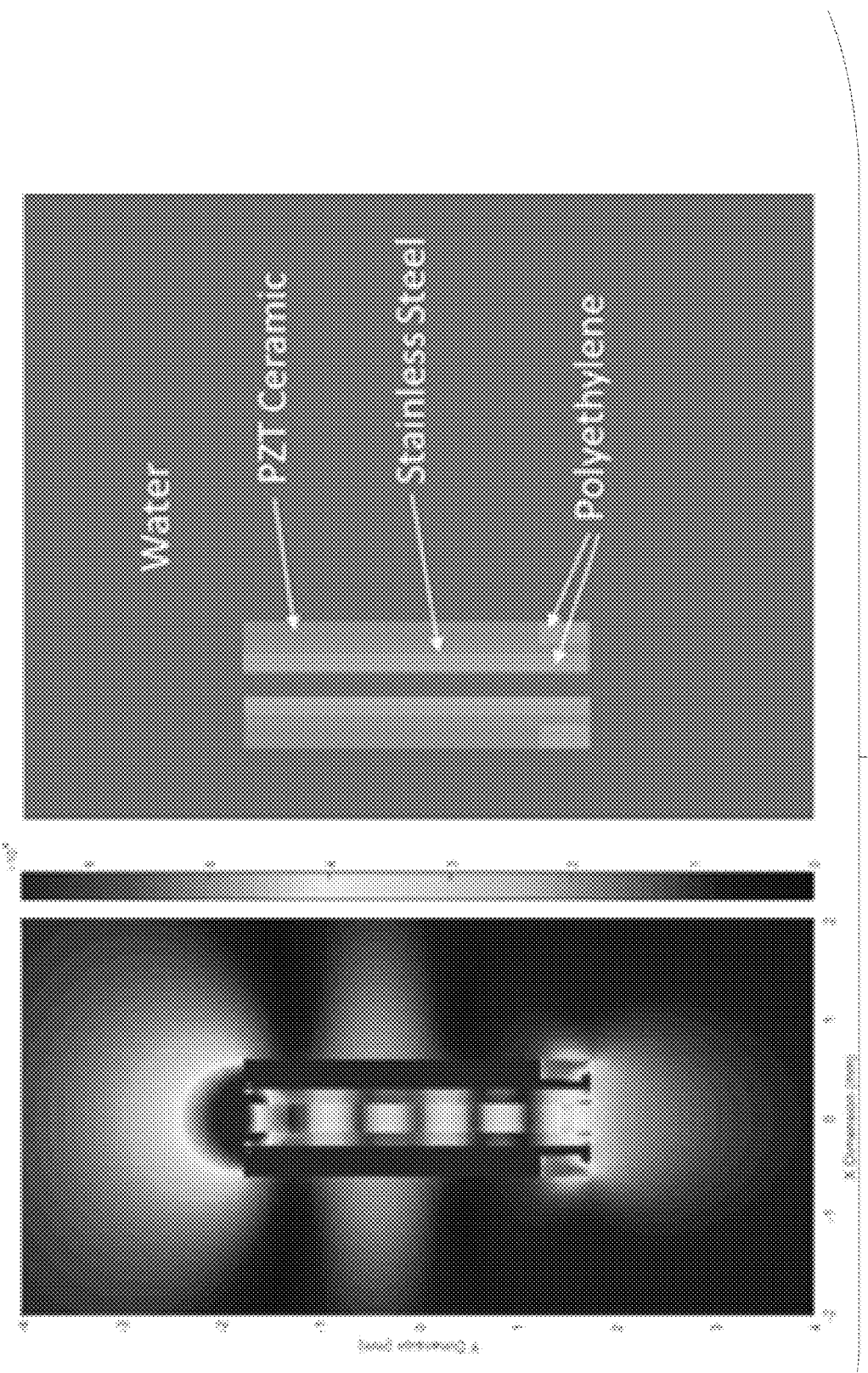
FIG. 5 is an image of a non-limiting example of simulations of a design for the system.

Referring to FIG. 5, a non-limiting example simulations of a more complex situation incorporating other design elements is shown. Left: Pressure map from PZFlex simulation demonstrating a selection of sample features that can be modeled. Right: Labeled model of simulated parts. Note that the design elements have affected the resultant field, in particular having proportionally more energy projected forwards (distal tip is at top). A primary purpose of a 'backing element' is to have a favorable impact on the ultrasound energy in terms of its therapeutic use. In the example shown in FIG. 5, the material is polyethylene. In this example, it can be observed that the combination of the backing element, transducer geometry, outer sheath, and inner sheath (there can be more than one, as well as adhesive materials) has impacted the degree of forward propagated ultrasound.

This is an advantageous design criteria since, in general, achieving higher pressure amplitudes in a forward propagating manner is desirable.

Figure 6A:
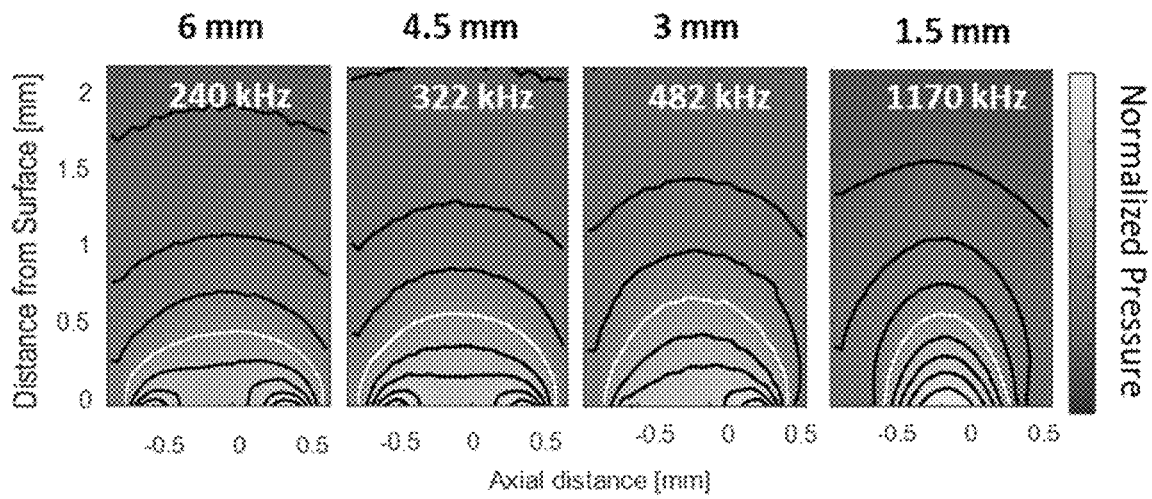
FIGS. 6A-6C show examples of pressure distributions.
Figure 6B:
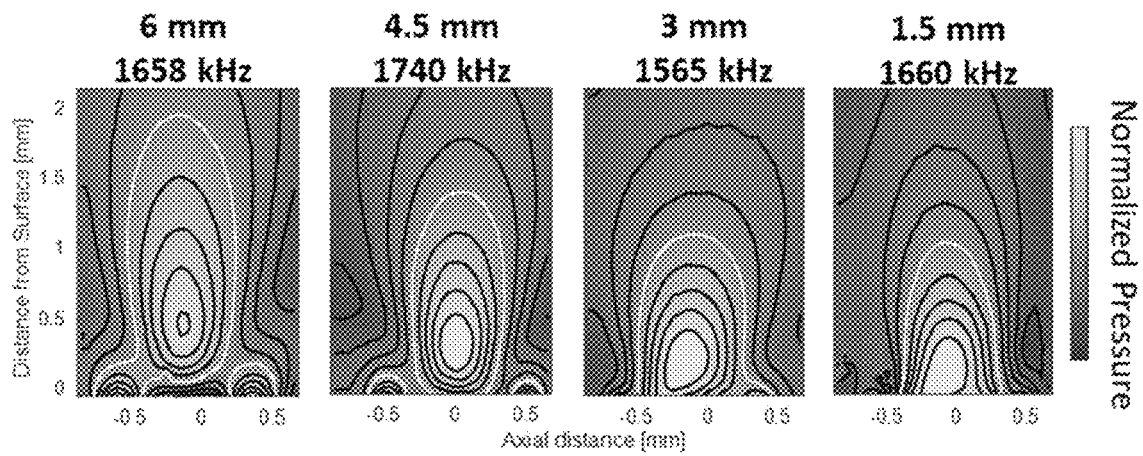
Figure 6C:
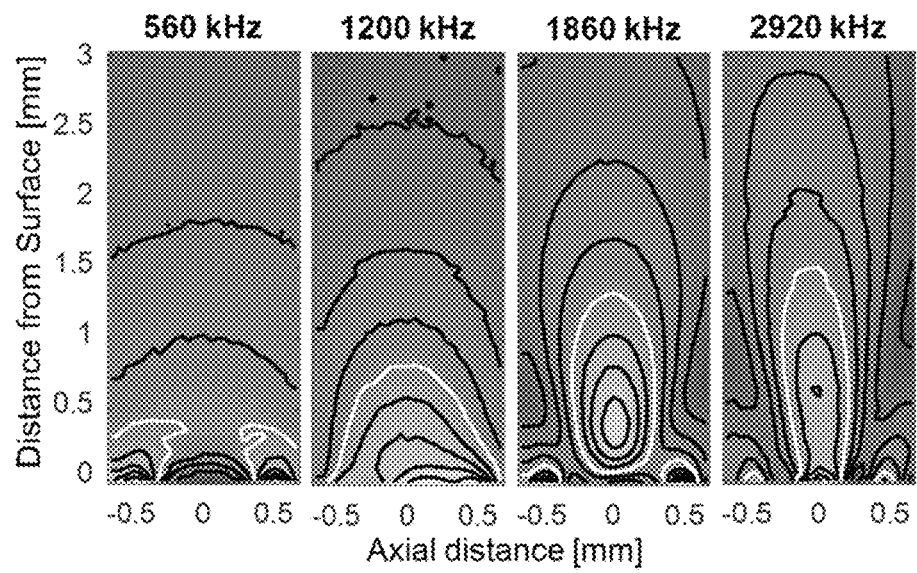

Referring to FIGS. 6A-6C, non-limiting examples of pressure fields external to hollow cylindrical transducers of different lengths are shown. In the examples shown in FIGS. 6A and 6B, the transducer used had 1.2 mm inner and 0.8 mm radii and were composed of PZT4 material. The frequency of stimulation corresponds to the length mode for FIG. 6A and a higher mode (e.g., a circumferential mode) for FIG. 6B. In FIG. 6C, for a fixed transducer length of 2.5 mm, pressure fields are shown when the transducer is stimulated at different frequencies that produced local maxima in pressures. The higher frequencies in this case were projected further out, which may be advantageous for the treatment of occlusions.

Figure 7:
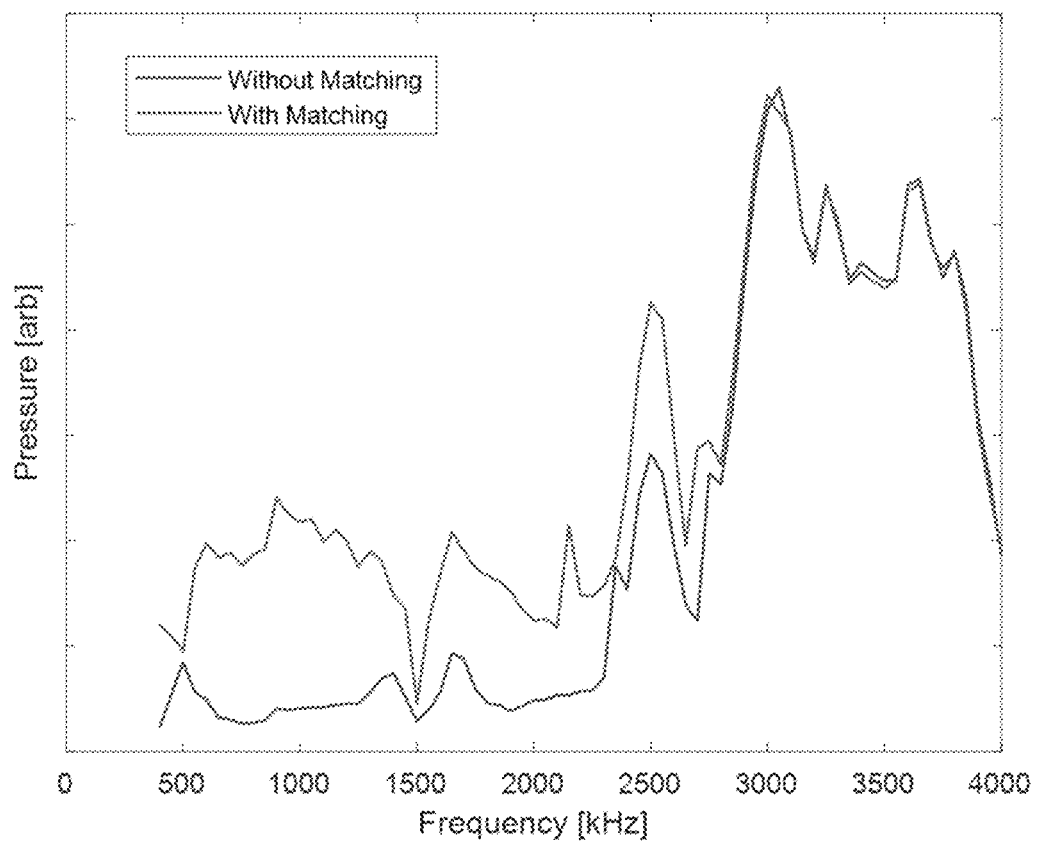
FIG. 7 shows pressure measurements 500 micrometers from the face of a 3 mm transducer, comparing the effect of impedance matching.

In FIG. 7, a non-limiting example of pressure measurements (at 0.5 mm from the face of a 2.5 mm length transducer) are shown as a function of frequency, both with and without electrical matching. A complex pressure pattern can be seen, which is in part due to frequency dependent diffraction, as well as the presence of different resonances and their associated radiation patterns. The electrical matching can be seen to significantly improve the transmitted pressure levels. The matching in this example was achieved with a computer controlled dynamic matching circuit. In some configurations, dynamic switching of impedance matching can be employed to take advantage of radiation patterns associated with different frequencies, such as by inducing cavitation internal to the transducer, using radiation forces, and projecting the beam forward with one for more frequencies to exploit different spatial patterns.

Figure 8A:
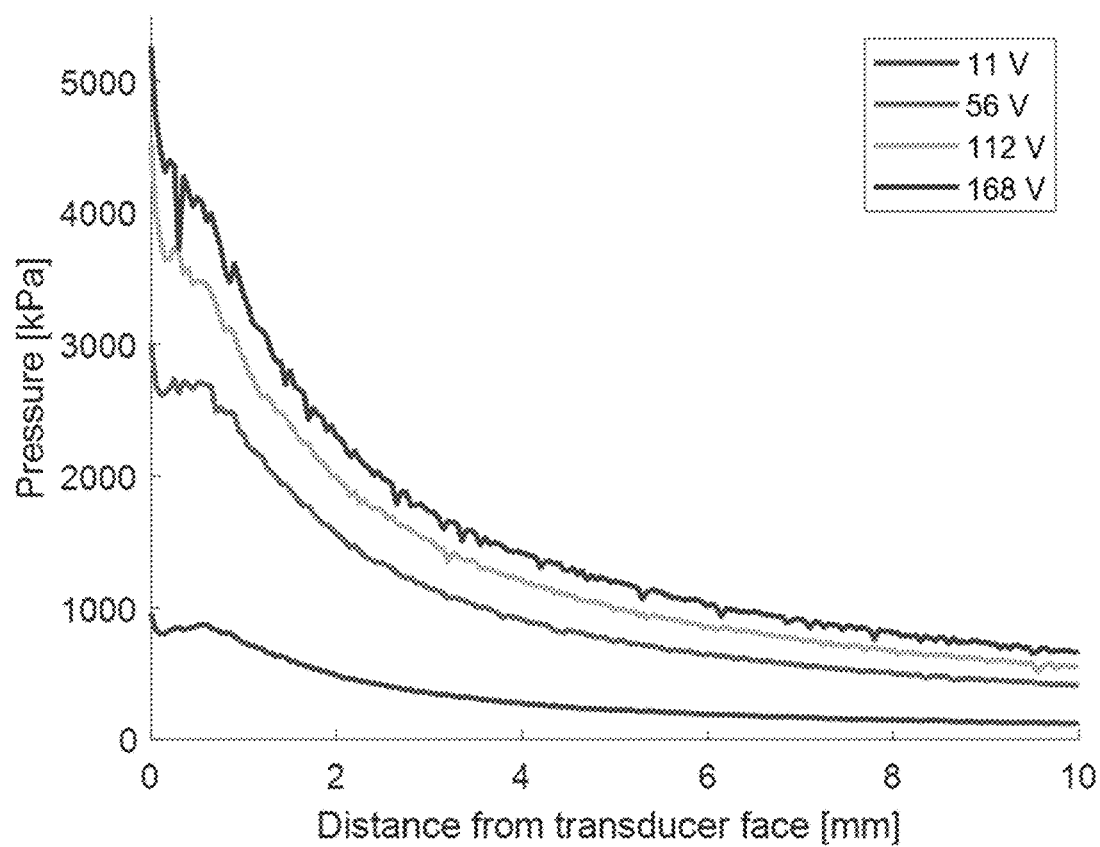
FIGS. 8A and 8B show examples of pressure measurements using a 2.5 mm element with a sheath inside excited at 2.9 MHz.
Figure 8B:
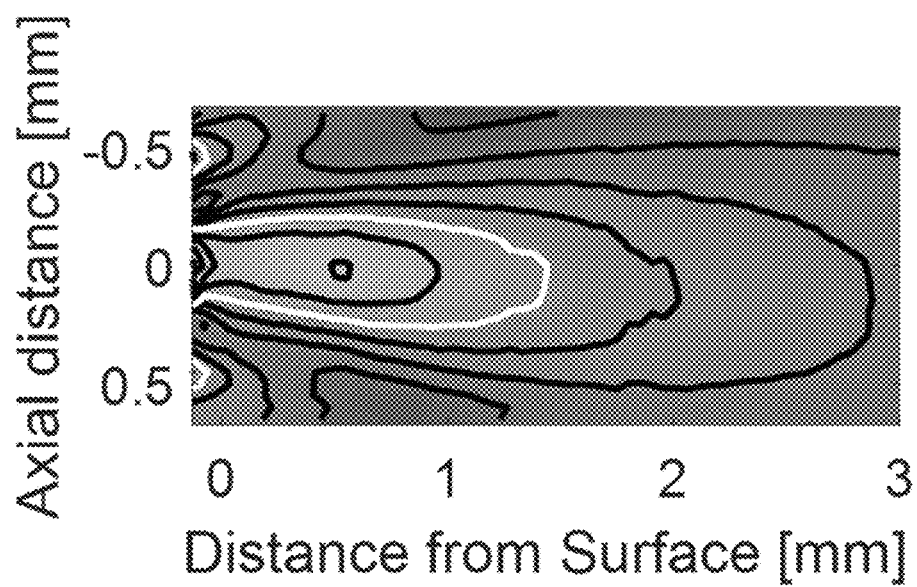

In FIGS. 8A and 8B, a non-limiting example is shown for a 2.5 mm length transducer, containing a metal sheath of wall thickness of approximately 0.1 mm and outer diameter around 0.75 mm to fit, in contact with the inner electrode, within the transducer. FIG. 8A shows the pressure, measured by a hydrophone, as a function of distance along the axis of symmetry as a function of applied voltage. A 2D cross section or normalized pressure distribution is also shown in FIG. 8B. It can be seen that pressures up to 5 MPa were obtained in this example, and exceeded 1 MPa until about 6 mm.

Figure 9A:
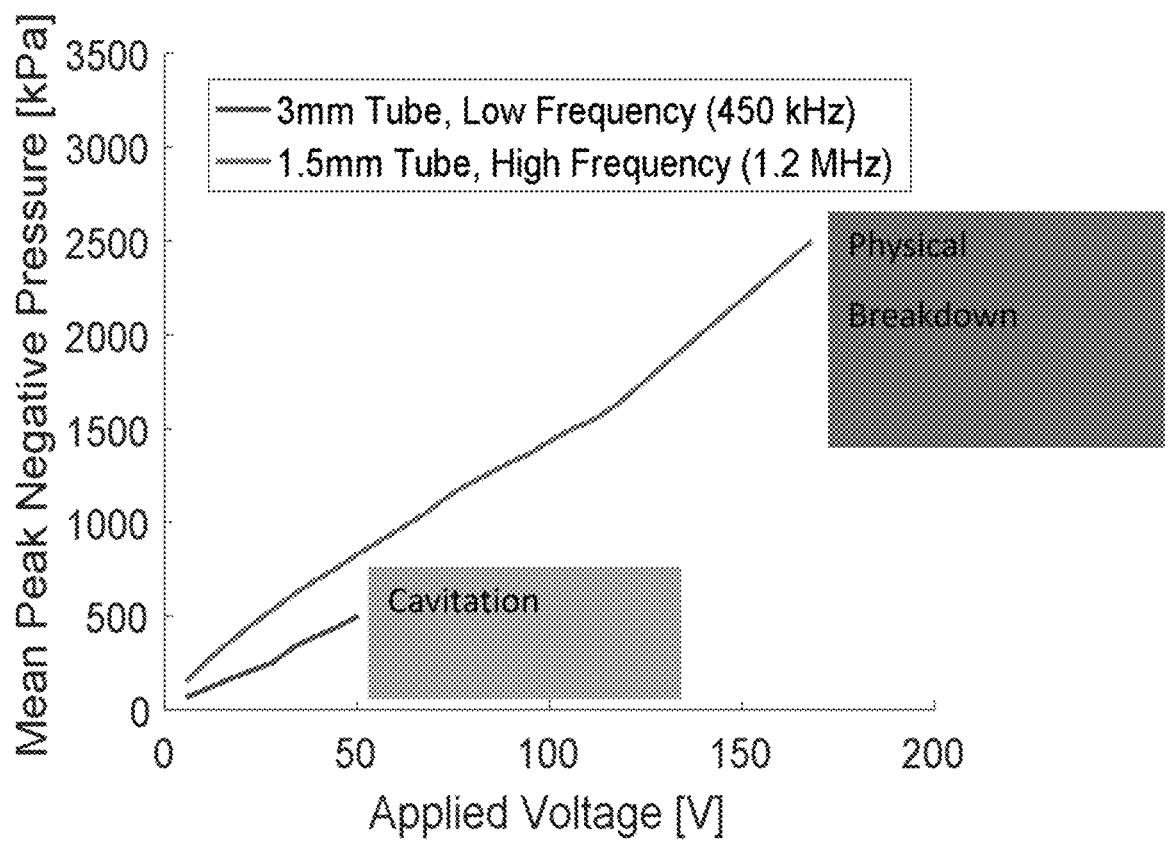
FIGS. 9A and 9B show more examples of pressure measurements.
Figure 9B:
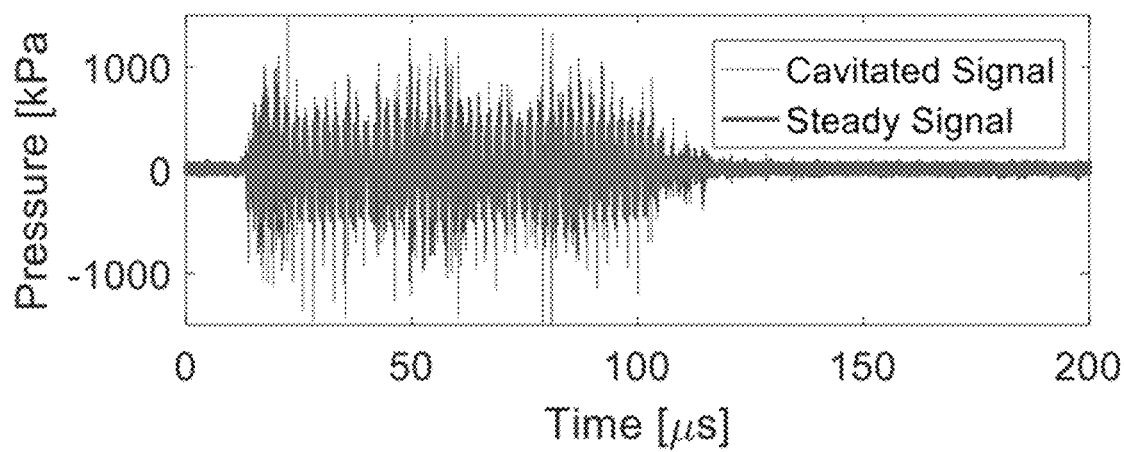

In FIGS. 9A and 9B, a non-limiting example of data from two transducers is shown: one 1.5 mm (stimulated at 1.2 MHz) and a second 3 mm in length (stimulated at 450 kHz). FIG. 9A shows the measured pressure (at 0.5 mm from transducer face) as a function of applied voltage. The 1.5 mm tube shows that pressures in excess of 2.5 MPa were obtained, after which point the applied voltage resulted in a physical breakdown of the transducer. Sufficiently high voltages can result in visible and irreversible mechanical damage, as well as de-poling. These may vary as a function of transducer material, geometry, dimensions, and boundary materials (e.g. sheath and attachment methods). Design approaches that mitigate these effects to permit higher applied voltages are an advantageous aspect of the system designs described in the present disclosure.

The data for the 3 mm transducer stimulated at the lower frequency indicate that, as the pressure (at 0.5 mm) approached 500 kPa, cavitation began to occur, as evidenced by an erratic hydrophone signal, as shown in FIG. 9B. This occurred when degassed water was flowed through the tube. This demonstrates that cavitation can be induced in the absence of externally introduced cavitation seeds. An examination of the finite element simulations suggests that the cavitation could be both internal to the tube as well as near its distal face. It is contemplated that the use of lower frequencies likely facilitated this occurrence, and could be produced at less than 0.5 MHz in a range of transducer lengths, with or without an inner sheath. This type of cavitation can be employed to degrade vascular occlusions. The frequency and transducer geometry can be used as variables in tuning the implementation. The external forward projected energy and internal ultrasound field are also relevant factors. A separate point relating to FIG. 9A is that when this type of cavitation was occurring, the forward projected pressure could be limited. Thus, for some applications, where a forward projected field is more important, such cavitation may be avoided, for example by the use of a higher frequency.

Figures 10A, 10B:
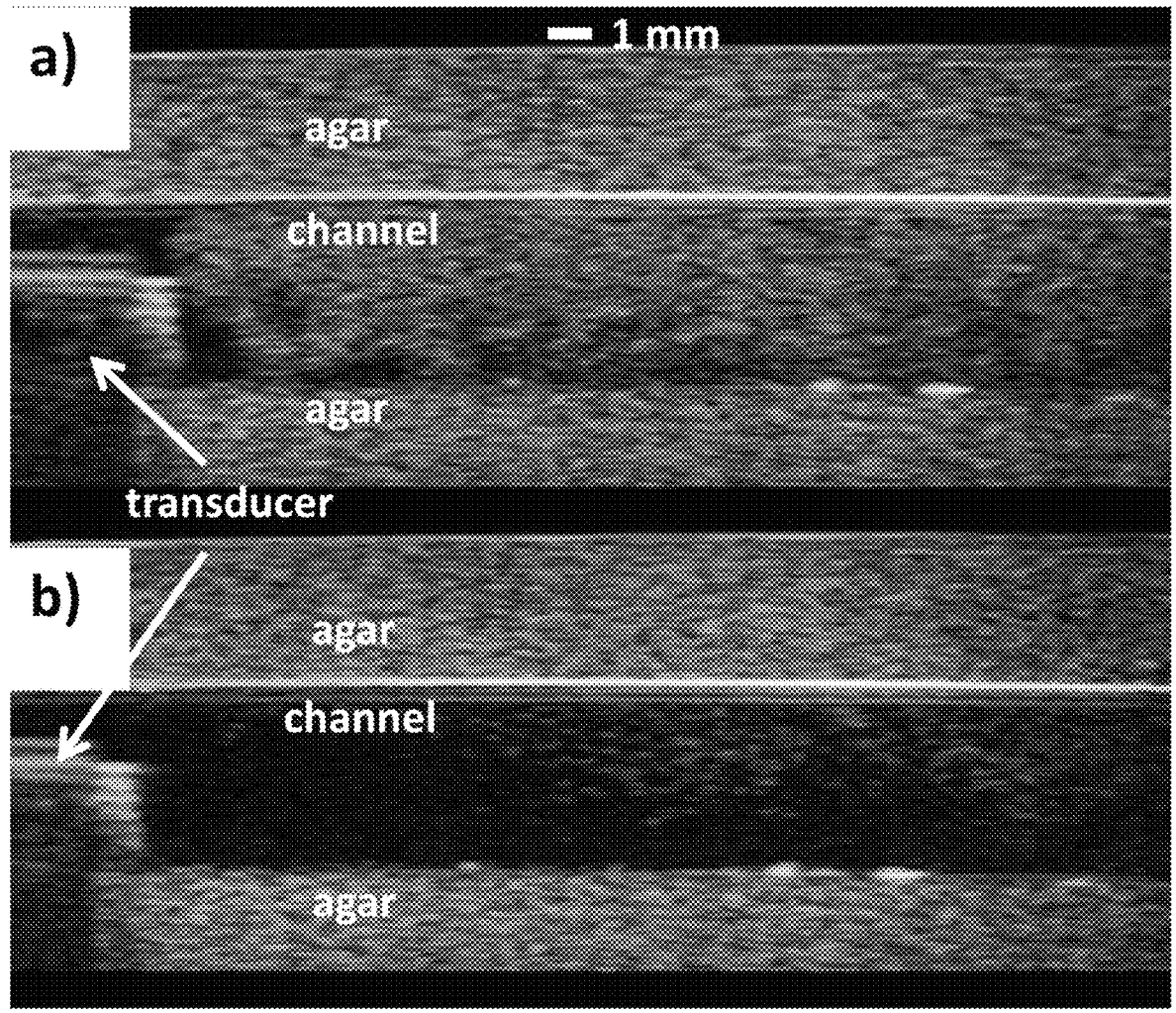
FIGS. 10A and 10B show example ultrasound images of a transducer (with sheath) mounted in a catheter tip. The transducer is shown as inducing destruction of microbubbles within a vessel phantom. Microbubbles were introduced through the transducer channel. The vessel phantom channel was cast in scatterer doped agarose (FIG. 10A) after injection of microbubbles and (FIG. 10B) subsequent microbubble destruction after sonication is evident as a profound reduction in echoes from within the channel. Exposures: 1 second duration, 0.1% duty cycle, 1.85 MHz, 56 Vpk-pk, 2.5 mm element @ 1.85 MHz.

In a non-limiting example, a 2.5 mm transducer, with an inner sheath, placed at the tip of a delivery catheter was used to disrupt microbubbles. A vessel (~4 mm diameter) channel was formed within a tissue mimicking phantom. The channel was filled with a diluted suspension of (Definity™) microbubbles that were introduced by flowing through the transducer hole. As shown in FIGS. 10A and 10B, microbubble echoes in the channel were depleted to a distance approaching at least 1 cm after an exposure of 1 s duration (1.85 MHz, 0.1% duty cycle, 56 v applied voltage peak to peak). This shows the ability of a transducer package to cavitate clinically approved microbubbles to the point that they are destroyed.

Figure 11:
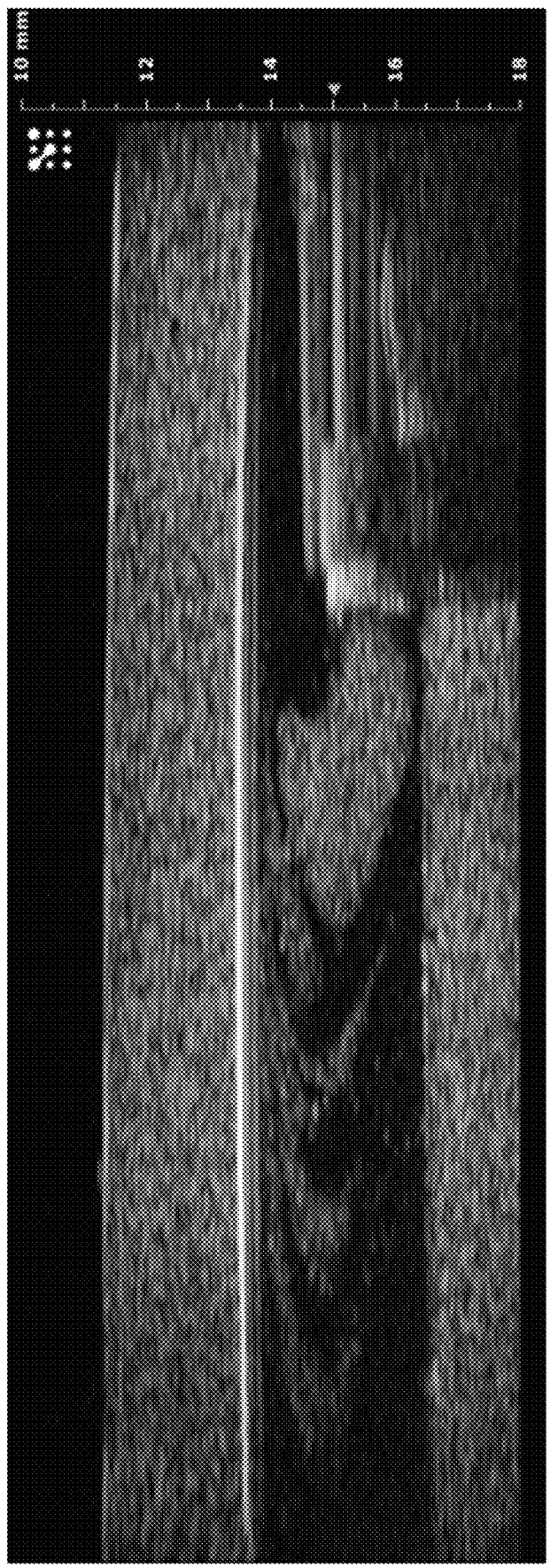
FIG. 11 shows an example ultrasound image of a transducer (with sheath) mounted in a catheter tip. The transducer is shown inducing destruction of microbubbles within a vessel phantom. Microbubbles were introduced through the transducer channel. In this case, microbubbles were flowed through the transducer while pulsing (1 ms, 1.85 MHz) occurred at 1 s intervals for 5 s. A striped pattern is shown as evolving, which is consistent with microbubble destruction within the tube and adjacent to the transducer face.

A second example of a phantom experiment is shown in FIG. 11. In this case, the experiment was to flow the suspension through the transducer and pulse (1 ms length, 1.85 MHz) every second for 5 seconds. This resulted in a striped pattern that was due to destruction of microbubbles within and immediately in front of the transducer. This highlights the potential for, in some system configurations, to have flow integrated into the control system, along with cavitation detection to ensure that microbubbles (or whatever cavitation agent is employed) are present distal to the transducer tip.

Figure 12:
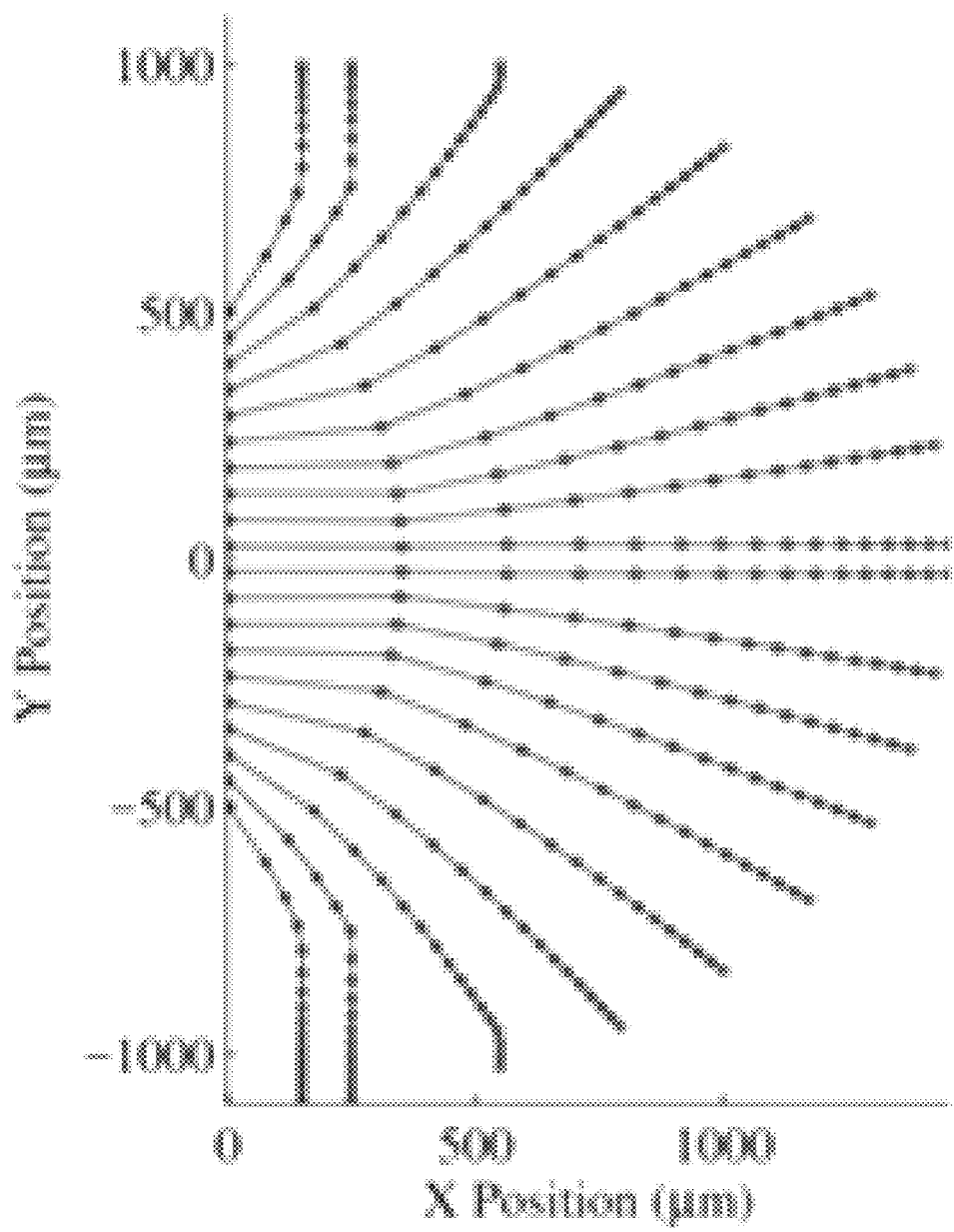
FIG. 12 is a graph showing non-limiting example results for simulations to predict radiation force induced by ultrasound beams.

Referring to FIG. 12, a non-limiting example result for simulations to predict radiation force induced MB motion in complex US beams is shown. In one configuration, radiation forces may be used to facilitate treatments. Primary radiation forces refer to a force experienced by an object (e.g., bubble in a fluid) that pushes it in the direction of ultrasound propagation. An example simulation is shown in FIG. 12, where bubbles initially at the catheter tip have been displaced away from the tip through primary radiation forces. This effect may be advantageous to assist in positioning the bubbles at the occlusion interface, and that particular exposure bursts may be advantageous for this portion of the treatment process. In this example, a series of 6 micron MBs are initially adjacent to the surface of a 1/0.5 mm cylinder and rapidly translate when being subjected to fifteen 1 ms, 450 kPa bursts.

In some configurations, exposure sequences can be multistage in recognition that bubbles will be subjected to energy within the tube, displaced within the beam, and then at the occlusion surface. These stages can involve the use of different frequencies and amplitudes. This is, in part, in recognition of the multitude potential purposes of the devices and applications described in the present disclosure. For example cavitation internal to the tube may be desired, and this may require a certain frequency and amplitude. This cavitation could be to degrade thrombus present, or to convert liquid phase droplets, or to form bubbles, or for other reasons. Radiation forces, if used, may require other frequencies and amplitudes, which may change during the course of exposure in recognition of the frequency dependent pattern present. This may mean multiple frequencies are sent at once time (with different amplitudes or with time-varying envelope amplitudes), in sequence (with or without pauses between), or in a "chirped" frequency mode.

In addition, multiple frequencies may be employed to generate cavitation for therapeutic purposes distal to the catheter tip. This is in recognition that different frequencies will produce different spatial patterns of ultrasound, and that can provide a way to expose different regions distal to the catheter. Further, varying these as a function of time is considered, as the spatial distribution of bubbles will vary with time (including the time scales of an exposure pulse). Further, the process of exposing may affect the pressure distribution of the field and a modification of the frequency and amplitude may be advantageous to account for this. For example, if a bubble cloud is initiated internal to the transducer, this could alter the forward projected ultrasound beam. In all of these cases, the manner in which the transducer is stimulated can be potentially controlled using information that has been collected relating to cavitation that is present. That is, cavitation feedback control can be used.

The use of a cylindrical transducer to induce cavitation within its body may also have configurations that would be a relevant addition to existing catheter based thrombolysis devices. The ability to cavitate within the transducer lumen (and/or project therapeutically relevant ultrasound distal from the catheter tip) and break up thrombus material that is being retrieved inside and distal to the tip may improve the retrieval speed through a reduction of resistance and thereby reduce the time required to resolve a vascular occlusion, or improve the degree of clot retrieval.

Variations of the hollow cylindrical geometry are also considered. For example having a taper (linear or otherwise), in the thickness (through a reduction if the inner or outer radii or both) of the transducer wall. This configuration could produce a field that is advantageous in terms of amplitude or spatial distribution, for initiating cavitation, radiation forces based transport, or exposing bubbles present near to or external to the catheter tip. In some instances, the lumen of the ultrasound catheter can also be off-center, such that the ultrasound transducer has a larger radial thickness on one side than the other. A variation of may be to have electrode patterns on the inner and/or outer surface that facilitate differences in the degree or timing of the oscillation amplitude or phase or other characteristic along the long axis of the transducer. For example, having more complete surface coverage at the proximal ends transitioning to more sparse coverage at the distal end. This could be accomplished with different patterns, and could be done with single wire connections to each face.

In other configurations, the use of two or more cylindrical transducers can be employed. These transducers could be immediately adjacent to each other and in contact and share common electrode connections. These configurations can be advantageous for altering or increasing the pressure output or ultrasound field. The transducers may also have different electrode connections (thereby requiring different wires and matching), that are separated in space and that can be stimulated at different frequencies and amplitudes. In some implementations, one transducer could be used to generate bubbles (or degrade thrombus) and the other could be used to generate forward projecting ultrasound and/or internally directed ultrasound. Alternatively, other field patterns could be generated in this manner.

In some implementations when there is an additional cylindrical transducer proximal to the tip transducer (or transducers), and it is being used to generate or manipulate bubbles, there may be side holes in the catheter between the proximal transducer and distal transducer(s). This would enable a portion of the bubbles to exit the catheter lumen (that holds externally introduced fluids) to be released within the vessel lumen proximal to the catheter tip, as well as through the tip. Such a configuration may produce a distribution of cavitation seeds that is advantageous for treating occlusions with ultrasound that can be emanated from the cylindrical transducer(s) at the tip.

In some configurations of the system, when there are one or more hollow cylindrical transducers at or near the catheter tip, there may be one or more side holes in the catheter between the proximal transducer and distal transducer(s). This would enable a portion of the cavitation seeds and or enzymes or drugs to exit the catheter lumen (that holds externally introduced fluids) to be released within the vessel lumen proximal to the catheter tip, as well as through the tip. Such a configuration may produce a distribution of cavitation seeds that is advantageous for treating occlusions with ultrasound that can be emanated from the cylindrical transducer(s) at the tip.

Catheter based ultrasound for treating vascular walls (e.g. atherosclerotic plaques) using cavitation of microbubbles has been investigated (e.g. U.S. Pat. No. 8,622,911 B2). It is necessary, or preferred to have bubbles injected in the vicinity of the ultrasound transducer situated near a catheter tip, where the ultrasound is directed in the radial direction. Previous work has attempted to do this through microfluidics approaches [new ref 3]. The use of a cylindrical element upstream of the therapeutic catheter to generate bubbles is considered here, where nuclei such as droplets or surfactant in solution is flowed through the cylinder and used to create cavitation. This may be accompanied by appropriate downstream holes in the catheter to permit release into the lumen. There may be separate lumens, to accommodate wiring associated with the distal ultrasound transducer, which may also include the capacity to rotate it.

Catheter based intravascular ultrasound imaging of microbubble agents has also been reported, which has applications for example in atherosclerotic plaque detection and risk stratification (U.S. Pat. No. 8,454,520). To date this has often entailed injecting bubbles upstream of the imaging catheter through a delivery catheter. Here we consider a configuration, similar to the preceding paragraph, wherein a cylindrical transducer is used to create bubbles within its lumen and these then translate distally within the catheter to either reach an exit port (e.g. holes in the side of the catheter) or at the end of the lumen. Multiple lumens are considered, with one being occupied by the IVUS wiring and possibly torque cable.

In another configuration, a cylindrical transducer is situated within a hollow tube catheter (for example a 'delivery' catheter used to deploy x-ray contrast material, with appropriate wiring to the external aspect of the system. Fluid within the catheter will be flushed with fluids (e.g. saline, radiopaque contrast material) which contain material (i.e. liquid phase droplets, albumin or other surfactant material) favorable to creating stabilized bubbles. The bubble will then exit the catheter thereby providing a local source for bubbles. These bubbles may be imaged with ultrasound, use exposed to ultrasound for therapeutic purposes (for example using an extracorporeal system). The catheter may be situated within blood vessels (e.g. cardiac, liver, cerebral, peripheral, kidney) such that bubbles are released into a relevant region of tissue. Therapeutic agents may also be delivered with the same catheter. For example chemotherapeutic agents (e.g. for TACE in the liver), radiotherapy agents, or stem cells or viral therapy or other compounds. Compounds that are already injected by catheter routes, and may benefit from microbubble mediated ultrasound therapy may benefit from this approach.

In other configurations, the use of cylindrical transducers are considered to generate bubbles within the context of an indwelling catheter. In this case, coupled with periodic fluid flow there can be released periodic timing controlled boluses of microbubbles, which can then circulate and be used for diagnostic (e.g. ultrasound imaging or pulse wave Doppler) or therapeutic (another ultrasound transducer extracorporeally or in some manner embedded in the body) purposes at a local or distal site.

Figure 13:
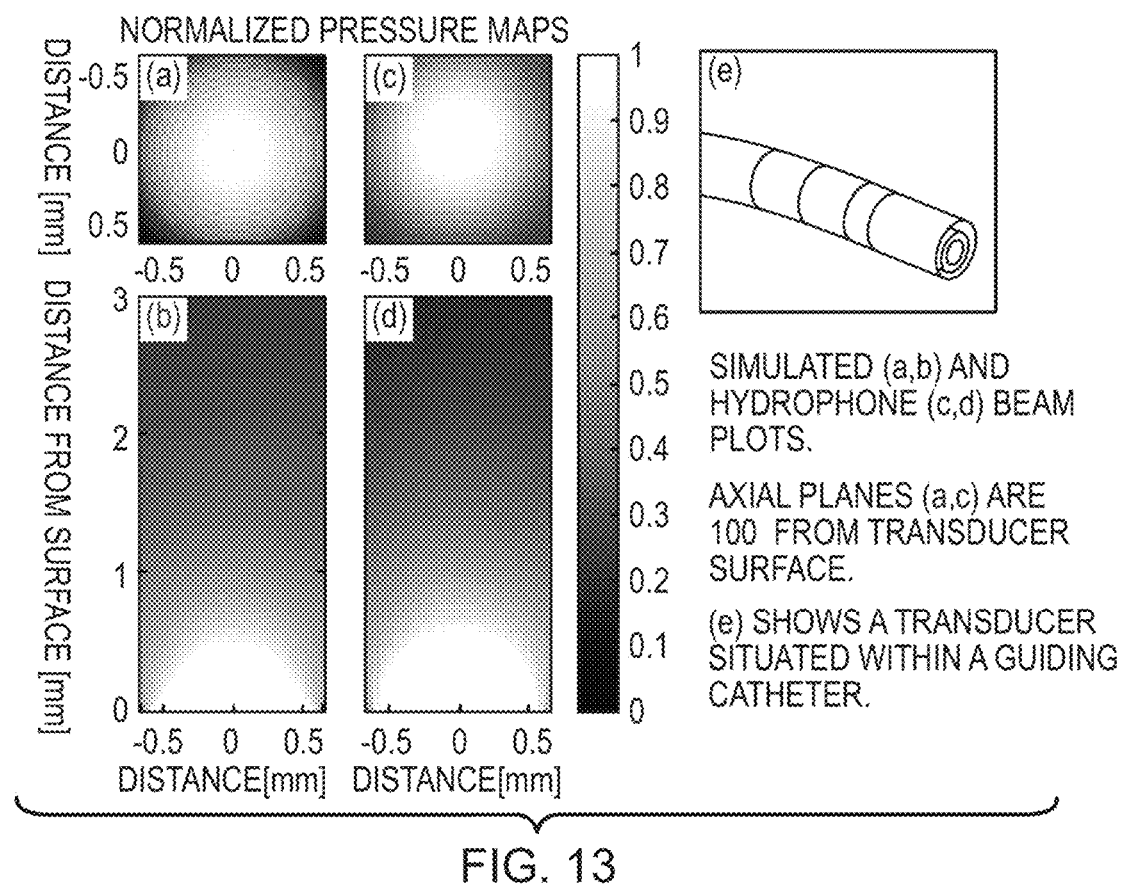
FIG. 13 is a graph and an image of one non-limiting example of data collected from a prototype device.

Referring to FIG. 13, one non-limiting example is shown of data collected from a prototype device. Note that e) is not the device but rather the transducer placed in a guide catheter for illustrative purposes.

In some configurations, there may be more than one lumen for all or a portion of the catheter length. This may enable the introduction of different fluids separately (e.g., cavitation seeds, flushing, drugs or enzymes) and or the separation of guide wires, "separators" (for thrombus), and electrical wiring. It may also permit the separation of aspiration functionality with the introduction of fluids and, for example, wires. Multiple lumens may also be associated with multiple control functionality for the system (e.g. each being under separate control of the system).

The present disclosure has described one or more preferred embodiments, and it should be appreciated that many equivalents, alternatives, variations, and modifications, aside from those expressly stated, are possible and within the scope of the invention.

The invention claimed is:

1. A system for delivering intravascular ultrasound therapy, the system comprising:
    a catheter extending from a proximal end to a distal end along a longitudinal axis and having a lumen extending therethrough;
    a cylindrical annular ultrasound transducer coupled to the distal end of the catheter and coaxial with the longitudinal axis of the catheter, the cylindrical annular ultrasound transducer having a lumen extending therethrough, the cylindrical annular ultrasound transducer being capable of excitation according to a plurality of vibrational modes, wherein excitation of a first mode generates inwardly propagating ultrasound energy within the lumen of the cylindrical annular ultrasound transducer and excitation of a second mode causes outward propagating ultrasound energy in a forward facing direction outward from a distal end of the cylindrical annular ultrasound transducer;
    a transmitter in electrical communication with the cylindrical annular ultrasound transducer;
    a pump in flow communication with the lumen of the cylindrical annular ultrasound transducer for flowing a media through the lumen of the cylindrical annular ultrasound transducer; and
    a controller operatively coupled to the pump and the transmitter, the controller being configured to perform operations comprising:
        controlling the pump to flow the media through the lumen of the cylindrical annular ultrasound transducer;
        controlling the transmitter to excite the first mode with sufficient energy to generate bubbles via cavitation within the media while the media resides within the lumen of the cylindrical annular ultrasound transducer; and
        controlling the transmitter to excite the second mode to induce oscillations of the bubbles after the bubbles emerge from the distal end of the cylindrical annular ultrasound transducer, for delivering therapy to a vascular occlusion residing beyond the distal end of the cylindrical annular ultrasound transducer.

2. The system of claim 1, wherein the lumen of the catheter and the lumen of the cylindrical annular ultrasound transducer are both sized to allow passage of a guidewire therethrough.

3. The system of claim 1, wherein the media comprises a therapeutic agent configured to accelerate one of thrombolysis, softening of chronic total occlusions, softening of plaque, or tissue removal.

4. The system of claim 1, wherein the media comprises a therapeutic agent comprising at least one of an enzyme or a thrombolytic drug.

5. The system of claim 1, wherein the media comprises cavitation nuclei or cavitation precursors, and wherein the first mode is excited with sufficient energy to generate bubbles via activation of the cavitation nuclei or cavitation precursors within the media while the media resides within the lumen of the cylindrical annular ultrasound transducer.

6. The system of claim 1, wherein the transmitter is programmed to cause the cylindrical annular ultrasound transducer to generate ultrasound using pulse lengths between 0.1 microseconds and 100 seconds.

7. The system of claim 1, wherein the transmitter is programmed to cause the cylindrical annular ultrasound transducer to generate ultrasound using pulse intervals between 0.1 microseconds and 100 seconds.

8. The system of claim 1, wherein the transmitter is programmed to cause the cylindrical annular ultrasound transducer to generate ultrasound using one or more pulses each comprising one or more frequencies that correspond to distinct resonant modes for the cylindrical annular ultrasound transducer.

9. The system of claim 1, wherein the transmitter is programmed to cause the cylindrical annular ultrasound transducer to generate ultrasound using sequences of pulses that differ in at least one of frequencies or amplitudes.

10. The system of claim 1, wherein the transmitter is programmed to cause the cylindrical annular ultrasound transducer to generate ultrasound using pulses with at least one of a time-varying frequency or a time-varying amplitude during a duration of the pulse.

11. The system of claim 1, wherein the transmitter is programmed to drive the cylindrical annular ultrasound transducer to generate ultrasound using at least one of voltage spikes, sinusoidal voltage waves, square voltage waves, fixed frequency voltage waves, variable frequency voltage waves, variable amplitude voltage waves, or variable phase voltage waves.

12. The system of claim 1, wherein the media comprises one or more of enzymes, drugs, saline, and x-ray contrast media.

13. The system of claim 1, wherein the pump is a first pump and the media is first media, the system further comprising an additional pump in flow communication with the lumen of the cylindrical annular ultrasound transducer for flowing an additional media through the lumen of the cylindrical annular ultrasound transducer, wherein the controller is operably coupled to the additional pump and configured to control the additional pump to adjust flow of the additional media through the lumen of the cylindrical annular ultrasound transducer.

14. The system of claim 1, further comprising an aspiration device in fluid communication with the cylindrical annular ultrasound transducer for applying suction through one of the lumen of the catheter, the lumen of the cylindrical annular ultrasound transducer, and an additional channel formed in the catheter adjacent the distal end of the catheter.

15. The system of claim 14, wherein the controller is operably coupled to the aspiration device and configured to control the aspiration device to apply suction on one of an intermittent or continuous basis.

16. The system of claim 1, further comprising an impedance matching circuit in communication with the cylindrical annular ultrasound transducer and configured to dynamically adjust electrical impedance matching in order to facilitate frequency and amplitude changes in ultrasound exposure pulses.

17. The system of claim 1, wherein the cylindrical annular ultrasound transducer has an outer diameter between 0.2 mm and 20 mm and a length between 0.2 mm and 20 mm.

18. The system of claim 1, further comprising a plurality of electrodes, the plurality of electrodes being coupled to at least one of an inner surface of the cylindrical annular ultrasound transducer, the outer surface of the cylindrical annular ultrasound transducer, or combinations thereof.

19. The system of claim 18, wherein the plurality of electrodes are arranged to cover both the inner surface of the cylindrical annular ultrasound transducer and the outer surfaces of the cylindrical annular ultrasound transducer.

20. The system of claim 18, wherein the plurality of electrodes are arranged in one or more spatial patterns that are so arranged in order to create selected transducer oscillation characteristics.

21. The system of claim 1, wherein the cylindrical annular ultrasound transducer is sized and shaped such that a thickness of the cylindrical annular ultrasound transducer varies along the longitudinal axis.

22. The system of claim 1, wherein the lumen of the cylindrical annular ultrasound transducer is radially offset from a radial center of the cylindrical annular ultrasound transducer.

23. The system of claim 1, wherein the cylindrical annular ultrasound transducer is a first cylindrical annular ultrasound transducer, the system further comprising a second cylindrical annular ultrasound transducer arranged adjacent the distal end of the catheter, the second cylindrical annular ultrasound transducer having a lumen extending therethrough.

24. The system of claim 23, wherein the second cylindrical annular ultrasound transducer is coaxial with the longitudinal axis of the catheter and coupled to the first cylindrical annular ultrasound transducer in a stacked arrangement.

25. The system of claim 23, wherein the first cylindrical annular ultrasound transducer and the second cylindrical annular ultrasound transducer are in communication with a transmitter that is configured to independently stimulate the first cylindrical annular ultrasound transducer and the second cylindrical annular ultrasound transducer.

26. The system of claim 1, further comprising a receiver in communication with the cylindrical annular ultrasound transducer and the controller, and wherein the cylindrical annular ultrasound transducer is operable to detect ultrasound signals representative of bubble activity and communicate the ultrasound signals as ultrasound signal data to the receiver.

27. The system of claim 26, wherein the cylindrical annular ultrasound transducer comprises a transmit portion and a receive portion, and wherein the receive portion is in communication with the receiver.

28. The system of claim 26, wherein the controller is configured to adjust operation of the cylindrical annular ultrasound transducer in response to the ultrasound signal data.

29. The system of claim 26, further comprising a pump in fluid communication with the catheter and a controller in communication with the receiver and the pump, wherein the controller is configured to control operation of the pump to adjust flow of media through the lumen of the cylindrical annular ultrasound transducer in response to the ultrasound signal data.

30. The system of claim 1, further comprising a hydrophone array coupled to a distal end of the cylindrical annular ultrasound transducer.

31. The system of claim 1, further comprising a fiber optic probe arranged within the lumen of the cylindrical annular ultrasound transducer.

32. The system of claim 1, further comprising a diagnostic ultrasound transducer arranged within the lumen of the cylindrical annular ultrasound transducer.

33. The system of claim 1, wherein the catheter further comprises at least one additional lumen, wherein the at least one additional lumen extends one of partially or fully through a length of the catheter.

34. The system of claim 1, wherein at least one exit port is formed in the catheter at the distal end of the catheter, the at least one exit port extending from the lumen through an outer surface of the catheter.

35. The system of claim 1, wherein the controller is configured to adjust operation of the cylindrical annular ultrasound transducer in response to at least one of an electrical signal or a reflected power measured at the cylindrical annular ultrasound transducer.

36. The system of claim 1, wherein the first mode is a radial thickness mode and the second mode is a length mode.

37. The system of claim 36, wherein the cylindrical annular ultrasound transducer has an inner diameter corresponding to the wavelength of a resonant frequency (or odd multiples thereof) of the radial thickness mode, such that excitation of the radial thickness mode results in generation of an amplified pressure peak within a central portion of the lumen of the cylindrical annular ultrasound transducer due to constructive interference.

38. The system of claim 1, wherein the media is absent of cavitation nuclei and cavitation precursors.

39. The system of claim 1, wherein the media comprises a stabilizing compound suitable for stabilizing the bubbles by encapsulation of the bubbles with the stabilizing compound.

40. The system of claim 39, wherein the stabilizing compound comprises one or more of albumin and phospholipids.

41. The system of claim 1 wherein the controller is configured such that the first mode and the second mode are excited sequentially, with the first mode being excited prior to excitation of the second mode.

42. The system of claim 1 wherein the controller is configured such that the first mode and the second mode are excited simultaneously.

43. The system of claim 1 wherein the controller is configured to sequentially control the transmitter and the pump, such that the pump is controlled to eject the bubbles are from the distal end of the cylindrical annular ultrasound transducer after having controlled the transmitter to generate the bubbles within the lumen of the cylindrical annular ultrasound transducer.

44. The system of claim 1 wherein the controller is configured to perform sequential operations comprising:
(i) controlling the pump to flow the media into the lumen of the cylindrical annular ultrasound transducer;
(ii) controlling the transmitter to excite the first mode with sufficient energy to generate bubbles via cavitation within the media while the media resides within the lumen of the cylindrical annular ultrasound transducer;
(iii) controlling the pump to cause the bubbles to emerge from the distal end of the cylindrical annular ultrasound transducer; and
(iv) controlling the transmitter to excite the second mode to induce the oscillations of the bubbles after the bubbles emerge from the distal end of the cylindrical annular ultrasound transducer.

45. The system of claim 44 wherein the controller is configured to repeat the sequence of steps (i) to (iv) one or more times.

46. The system of claim 1 wherein the controller is configured to excite the cylindrical annular ultrasound transducer, prior to exciting the second mode to induce oscillations of the bubbles for delivering therapy to the vascular occlusion, such that bubbles are displaced away from the distal end of the cylindrical annular ultrasound transducer through primary radiation forces.

* * * * *